(12) United States Patent
Kalman

(10) Patent No.: US 9,642,686 B1
(45) Date of Patent: May 9, 2017

(54) METHOD AND SYSTEM FOR RECORDING CHARACTERISTICS OF THE OCCLUSAL ARCH OF A PATIENT USING A PORTABLE COMPUTING DEVICE

(71) Applicant: Whip-Mix Corporation, Louisville, KY (US)

(72) Inventor: Laszlo Kalman, Komoka (CA)

(73) Assignee: Whip-Mix Corporation, Louisville, KY (US)

( * ) Notice: Subject to any disclaimer, the term of this patent is extended or adjusted under 35 U.S.C. 154(b) by 66 days.

(21) Appl. No.: 14/728,340

(22) Filed: Jun. 2, 2015

Related U.S. Application Data

(60) Provisional application No. 62/006,703, filed on Jun. 2, 2014.

(51) Int. Cl.
*G06K 9/00* (2006.01)
*A61C 19/045* (2006.01)
*A61C 19/05* (2006.01)
*A61C 9/00* (2006.01)
*A61C 13/34* (2006.01)

(52) U.S. Cl.
CPC .......... *A61C 19/045* (2013.01); *A61C 9/0053* (2013.01); *A61C 13/34* (2013.01); *A61C 19/05* (2013.01)

(58) Field of Classification Search
CPC ........................ A61C 9/00; G06T 2207/30036
USPC ....... 382/118; 433/19, 42, 54, 190, 198, 214
See application file for complete search history.

(56) References Cited

U.S. PATENT DOCUMENTS

| | | | | |
|---|---|---|---|---|
| 5,691,799 A | * | 11/1997 | Ramachandran | A61B 3/11 33/200 |
| 8,013,853 B1 | * | 9/2011 | Douglas | A61C 7/002 345/420 |
| 2002/0081554 A1 | * | 6/2002 | Marshall | A61C 11/001 433/213 |
| 2005/0271996 A1 | * | 12/2005 | Sporbert | A61C 7/00 433/24 |
| 2007/0186711 A1 | * | 8/2007 | Oberle | F16F 15/265 74/460 |

(Continued)

FOREIGN PATENT DOCUMENTS

| | | | | | |
|---|---|---|---|---|---|
| JP | WO 2013132537 A | * | 6/2013 | ............ | A61C 11/00 |
| TW | 201302164 A | * | 1/2013 | ............ | A61C 19/04 |

*Primary Examiner* — Gregory F Cunningham
(74) *Attorney, Agent, or Firm* — Stites & Harbison, PLLC; David W. Nagle, Jr.; James R. Hayne

(57) ABSTRACT

An exemplary virtual facebow system comprises a software program which is run on a tablet or other portable computing device with a microprocessor, an internal memory component, an image capture device, and a display screen. The virtual facebow system is used to record characteristics of the occlusal arch of a patient including, but not limited to, the midline of the patient's face, the steepness and cant of the occlusal arch, as well as a record of which maxillary (upper) teeth make contact with which mandibular (lower) teeth. The recorded characteristics are then used to replicate the alignment of the patient's occlusal arch with the maxillary cast in a lab stand, and the maxillary cast can then be moved to an articulator for the production of customized dental prosthetics for the patient including, but not limited to, restorations and partial or full dentures.

10 Claims, 19 Drawing Sheets

(56) References Cited

U.S. PATENT DOCUMENTS

| | | | | |
|---|---|---|---|---|
| 2007/0262988 | A1* | 11/2007 | Christensen | G06T 15/08 |
| | | | | 345/424 |
| 2009/0177081 | A1* | 7/2009 | Joskowicz | A61B 90/13 |
| | | | | 600/426 |
| 2009/0274267 | A1* | 11/2009 | Mandelkern | A61B 6/145 |
| | | | | 378/39 |
| 2010/0145898 | A1* | 6/2010 | Malfliet | A61C 19/04 |
| | | | | 706/47 |
| 2012/0010533 | A1* | 1/2012 | Arnett | A61B 5/0064 |
| | | | | 600/590 |
| 2012/0040311 | A1* | 2/2012 | Nilsson | A61C 19/05 |
| | | | | 433/214 |
| 2013/0122468 | A1* | 5/2013 | Abrams | A61B 6/14 |
| | | | | 433/215 |
| 2013/0158958 | A1* | 6/2013 | Methot | A61C 13/0004 |
| | | | | 703/1 |
| 2013/0330684 | A1* | 12/2013 | Dillon | A61B 1/00039 |
| | | | | 433/29 |
| 2014/0170587 | A1* | 6/2014 | Kopelman | A61C 13/0004 |
| | | | | 433/24 |
| 2016/0000525 | A1* | 1/2016 | Inglese | A61C 7/002 |
| | | | | 433/214 |

* cited by examiner

METHOD AND SYSTEM FOR RECORDING CHARACTERISTICS OF THE OCCLUSAL ARCH OF A PATIENT USING A PORTABLE COMPUTING DEVICE

CROSS-REFERENCE TO RELATED APPLICATIONS

The present application claims priority to U.S. Provisional Patent Application Ser. No. 62/006,703 filed on Jun. 2, 2014, the entire disclosure of which is incorporated herein by reference.

BACKGROUND OF THE INVENTION

The present invention relates to facebow systems and methods of use thereof. A facebow is a device used by doctors, nurses, or technicians to position upper tooth casts on an articulator to accurately replicate the alignment of the patient's teeth. Although traditional facebow systems are an improvement in replicating the natural bite of the patient, they are oftentimes unwieldy to work with, requiring a patient to hold the facebow apparatus to their head, and in some instances, insert a portion of the facebow into the ear canal.

SUMMARY OF THE INVENTION

The present invention is a virtual facebow system and methods of use thereof.

An exemplary virtual facebow system made in accordance with the present invention comprises a virtual facebow software program, preferably in the form of an application (hereinafter "app") which is run on a tablet or other portable computing device with a microprocessor, an internal memory component (e.g., a hard drive or solid-state drive), an image capture device (e.g., a camera), and a display screen.

An exemplary virtual facebow system made in accordance with the present invention may also include a stand that is used to support the tablet or other portable computing device for initial recordation of certain characteristics of the occlusal arch of a patient.

An exemplary method in accordance with the present invention then uses the virtual facebow system to record characteristics of the occlusal arch of a patient including, but not limited to, the midline of the patient's face, the steepness and cant of the occlusal arch, as well as a record of which maxillary (upper) teeth make contact with which mandibular (lower) teeth.

An exemplary virtual facebow system made in accordance with the present invention may also include a clamp assembly that is used in conjunction with a universal occlusal stand to fix the position of the camera of a tablet or other portable computing device relative to a maxillary cast.

An exemplary method in accordance with the present invention then uses the recorded characteristics to replicate the alignment of the patient's occlusal arch with the maxillary cast in an articulator for the production of customized dental prosthetics for the patient including, but not limited to, restorations and partial or full dentures.

In the exemplary method of the present invention, a tablet with the virtual facebow app is positioned with its camera facing and directed at the teeth of a patient, and a real-time image of the patient as captured by the camera is displayed on the screen along with a set of crosshairs and a skull image overlaying the real-time image of the patient. With the patient sitting in an upright position and the patient's head level, an operator adjusts the position and orientation of the tablet, such that the real-time image displayed on the screen is a straight-on view of the patient's face, and the crosshairs displayed on the screen are aligned with the patient's front teeth, such that the incisal edge of the patient's teeth lines up with the horizontal line of the crosshairs, and the patient's facial midline follows the vertical line of the crosshairs. Once properly aligned, a photographic image of the patient's face (i.e., a face image) is captured and stored in the memory component of the tablet as part of a patient file.

After capturing and storing the face image, the operator now measures the size of the patient's maxillary central incisors, i.e., the two front upper teeth (or centrals) and enters the measured size of the maxillary central incisors into the facebow app. An image of two front teeth is now also displayed on the screen as part of the skull image and the size of the teeth on the screen is correlated to the entered size of the maxillary central incisors.

The face image is also displayed on the screen overlaying the skull image with the image of the two front teeth and the crosshairs. The operator adjusts the captured face image to align the face image with the skull image, using, in part, the image of the two front teeth (which are sized in accordance with the entered size of the patient's maxillary central incisors) that are displayed on the screen as part of the skull image. The operator can move and scale the face image to align it with the skull image until the teeth of the patient in the face image are approximately aligned with the two front teeth of the skull image. Once the face image is properly aligned with the skull image, a composite image is captured and stored in the memory component of the tablet as part of the patient file.

A tooth chart is then displayed on the screen of the tablet, and the operator visually inspects the patient's teeth and records which of the patient's maxillary (upper) teeth touch which of the patient's mandibular (lower) teeth. The identification of the "touching" teeth is also stored in the memory component of the tablet as part of the patient file. The resultant tooth chart can be later used to confirm the position of a maxillary cast and mandibular cast.

All of the collected information and data is now stored in the memory component of the tablet in the patient file. Specifically, the patient file includes all pertinent characteristics of the occlusal arch. The patient's midline and cant have been captured in relation to the crosshairs in the face image. Furthermore, the face image can be used to determine the steepness of the occlusal arch (i.e., the anterior posterior relationship).

The patient file, which contains all of the collected information and data, may be sent to or retrieved by a third party. Such collected information and data can then be used to replicate the alignment of the patient's occlusal arch with a maxillary cast in an articulator for the production of customized dental prosthetics for the patient. Advantageously, the patient file containing the characteristics of the occlusal arch of the patient may be sent to a third party for use on a different tablet or other portable computing device which has the facebow app. However, the same tablet used for the steps described above may also be used in the production of customized dental prosthetics for the patient. In either event, a tablet or other portable computing device with the virtual facebow app installed is used to carry out the following steps.

A universal occlusal stand is positioned on top of and secured to a mounting platform of a lab stand. Extending from the front of this mounting platform is a clamp assembly, which holds the tablet, and thus the camera of the tablet, in a fixed position relative to the universal occlusal stand. A maxillary cast for the patient is created by methods well-known in the art and is temporarily affixed to the adjustable plate of the universal occlusal stand, and the tablet is secured relative to the universal occlusal stand via the clamp assembly.

A real-time image of the maxillary cast on the universal occlusal stand as captured by the camera is displayed on the screen, along with a set of crosshairs. The face image, as retrieved from the patient file stored in the memory component of the tablet, is then also displayed, such that the horizontal line of the crosshairs is aligned with the incisal edge of the teeth of the face image, and the vertical line of the crosshairs is aligned with the facial midline of the face image. The real-time image of the maxillary cast and crosshairs overlays the face image, and the operator adjusts the plate of the universal occlusal stand until the real-time image of the teeth of the maxillary cast is aligned with the patient's teeth as shown in the face image.

Once the real-time image of the maxillary cast is substantially aligned with the crosshairs and the face image, a photographic image of the maxillary cast (i.e., a cast image) is captured and stored in the memory component of the tablet as part of the patient file.

The screen of the tablet now displays the cast image and the face image so the operator can verify the alignment of the cast image to the face image. The operator is now able to zoom in on the overlaying images to ensure the teeth of the maxillary cast are properly aligned with the teeth on the face image. If they are not properly aligned, the operator returns to the previous screen and adjusts the plate of the universal occlusal stand until proper alignment is achieved and verified. After proper alignment is achieved and verified, a composite image of the cast image and the face image is captured and stored in the memory component of the tablet as part of the patient file.

Thus, in an exemplary method in accordance with the present invention, at least five image files are now stored in as part of the patient file, along with other patient information, including: (i) a photographic image of the patient's face (i.e., the face image); (ii) a composite image of the face image and the skull image; (iii) the tooth chart; (iv) a photographic image of the maxillary cast (i.e., the cast image); and (v) a composite image of the cast image and the face image. These five image files can be permanently stored as part of a medical record and/or sent to a third party, such as a dentist or orthodontist, for use in future dental care for the patient.

DETAILED DESCRIPTION OF THE INVENTION

The present invention is a virtual facebow system and methods of use thereof.

An exemplary virtual facebow system made in accordance with the present invention comprises a virtual facebow software program which is run on a tablet or other portable computing device with a microprocessor, an internal memory component (e.g., a hard drive or solid-state drive), an image capture device (e.g., a camera), and a display screen. In this case, the virtual facebow software program is in the form of an application (hereinafter "app"), which can be downloaded to the portable computing device for example through the internet by way of an app store, such as Google Play™. (Google Play™ is a trademark of Google, Inc. of Mountain View, Calif.).

An exemplary virtual facebow system made in accordance with the present invention may also include a stand that is used to support the tablet or other portable computing device for initial recordation of certain characteristics of the occlusal arch of a patient, as further described below.

An exemplary method in accordance with the present invention then uses the virtual facebow system to record characteristics of the occlusal arch of a patient including, but not limited to, the midline of the patient's face, the steepness and cant of the occlusal arch, as well as a record of which maxillary (upper) teeth make contact with which mandibular (lower) teeth.

An exemplary virtual facebow system made in accordance with the present invention may also include a clamp assembly that is used in conjunction with a universal occlusal stand to fix the position of the camera of a tablet or other portable computing device relative to a maxillary cast.

An exemplary method in accordance with the present invention then uses the recorded characteristics to replicate the alignment of the patient's occlusal arch with the maxillary cast in an articulator for the production of customized dental prosthetics for the patient including, but not limited to, restorations and partial or full dentures.

Recording Patient Information and Characteristics

Figure 1:
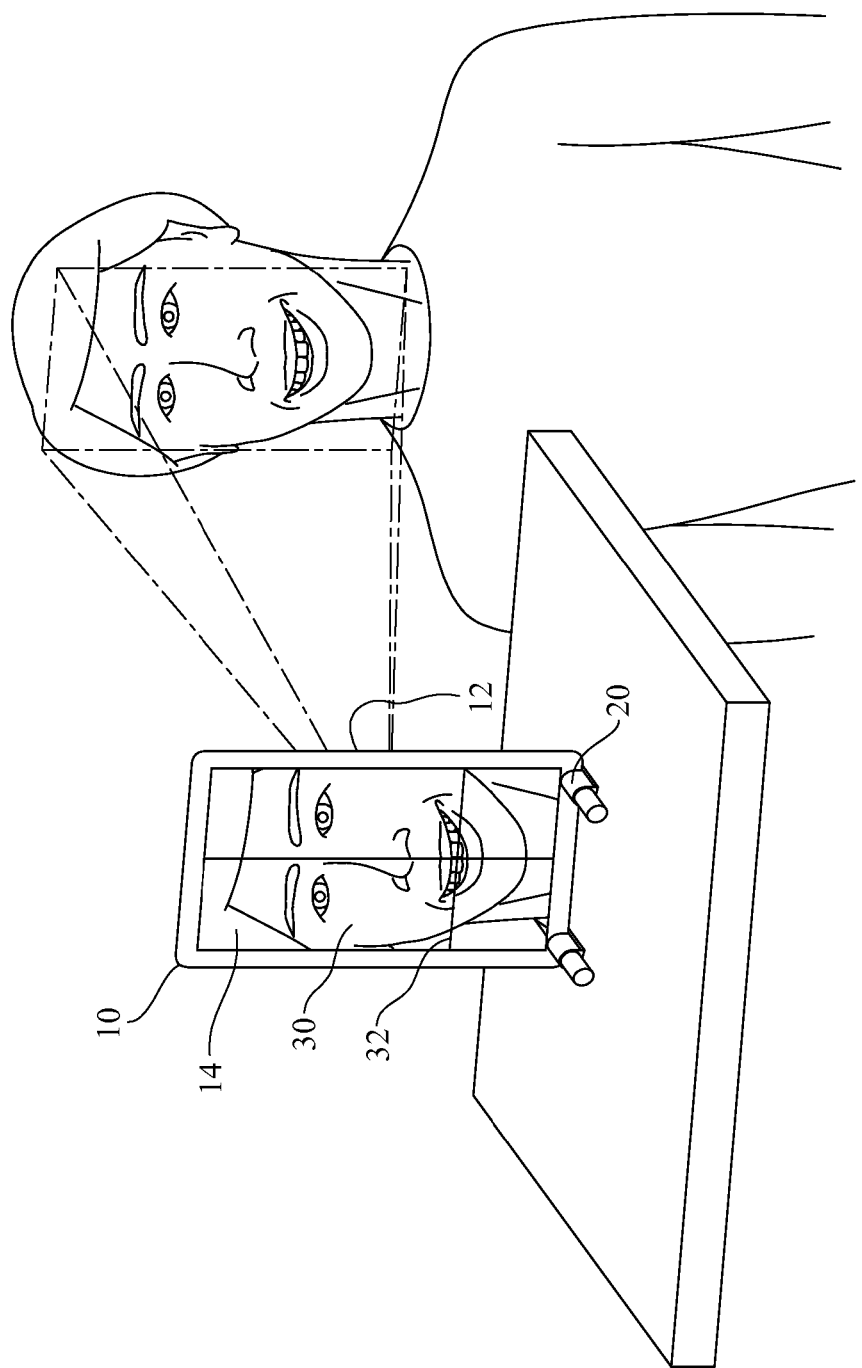
FIG. 1 is a perspective view of a tablet positioned with its camera facing and directed at the teeth of a patient in use in accordance with the systems and methods of the present invention.

FIG. 1 is a perspective view of a tablet 10 positioned with its camera 12 facing and directed at the teeth of a patient, while the screen 14 faces an operator, such as a doctor, nurse, or technician. In this example, the tablet 10 is supported by a stand 20. One suitable stand for use in supporting the tablet 10 is comprised of a pair of smartphone holders, namely Pholder 2.0 XSA-PHOH "Universal Mount for Tripod Smartphone Holder" manufactured and distributed by XSories of Biarritz, France.

Referring now to the flow chart of FIG. 2 (which also includes the continuation in FIG. 2A in the description that follows), once the tablet 10 or other portable computing device has been so positioned, an exemplary method for recording patient characteristics proceeds as follows.

Figure 2:
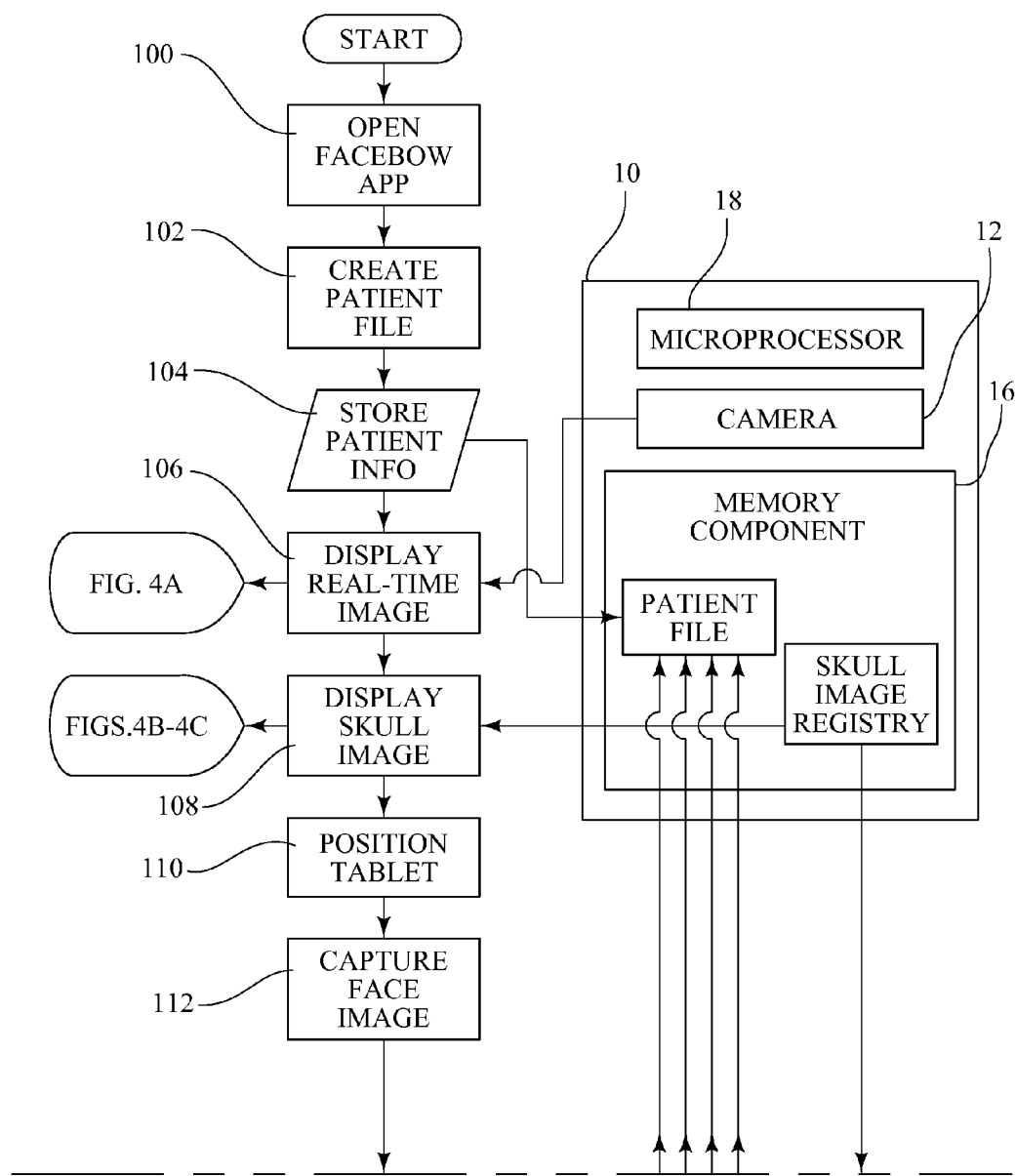
FIG. 2 is a flow chart of an exemplary implementation of the method of the present invention, illustrating the exemplary steps of recording patient information and characteristics.
Figure 2A:
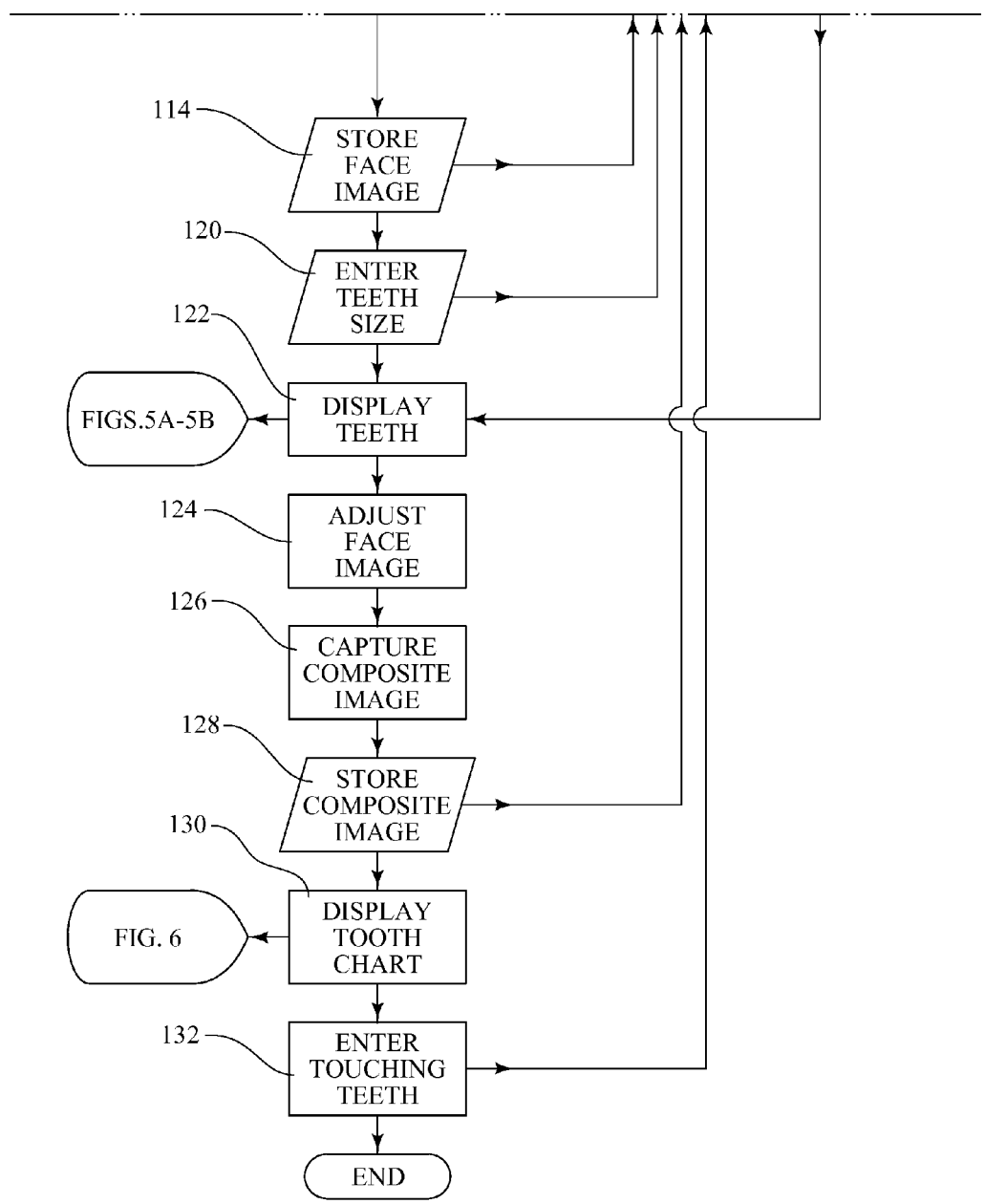
FIG. 2A is a continuation of the flow chart of FIG. 2.

First, as indicated by block 100 of FIG. 2, an operator, such as a doctor, nurse, or technician, opens the virtual facebow app on the tablet 10. In other words, the operator initiates the app, which causes computer-readable instructions stored in a memory component 16 of the tablet 10 to be executed by a microprocessor 18. Such computer-readable instructions can be coded into a computer-readable form using standard programming techniques and languages, and with benefit of the following description, such programming is readily accomplished by one of ordinary skill in the art.

Figure 3:
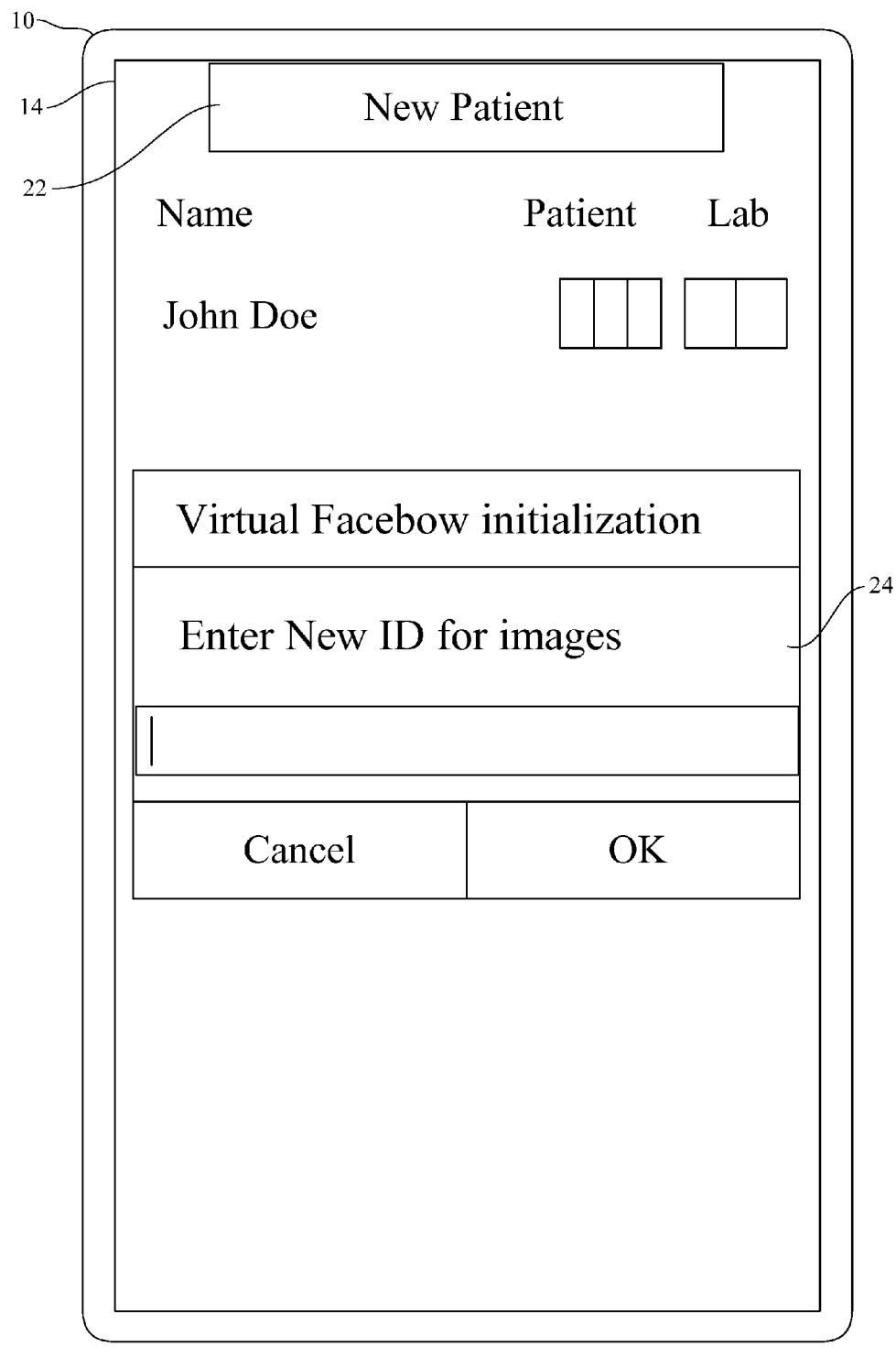
FIG. 3 is an exemplary screen shot displayed on the tablet of FIG. 1, prompting entry of certain patient information.

As indicated by block 102 of FIG. 2, the operator then creates a new patient file. Specifically, as prompted by the app via the screen 14 of the tablet 10, the operator enters certain patient information, including, for example, the patient's name and/or file number, in order to relate the subsequently collected data set to the particular patient. As shown in the exemplary screen shot of FIG. 3, a "New Patient" button 22 is displayed at the top of the screen 14 which, upon selection by the operator, generates a window in which the operator enters the relevant patient information, in this case, the "New ID for images" field 24. Such patient information is stored in the memory component 16 of the tablet 10, as indicated by block 104 of FIG. 2.

As indicated by block 106 of FIG. 2, after the patient information is entered and stored in the memory component 16, a real-time image 30 of the patient as captured by the camera 12 is displayed on the screen 14. Also displayed on the screen 14 is a set of crosshairs 32 (i.e., a vertical line and a horizontal line which intersect at a central position on the screen 14), which serve as a facial alignment image, as further described below. Such a real-time image 30 and a set of crosshairs 32 is shown in FIG. 1.

Figure 4A:
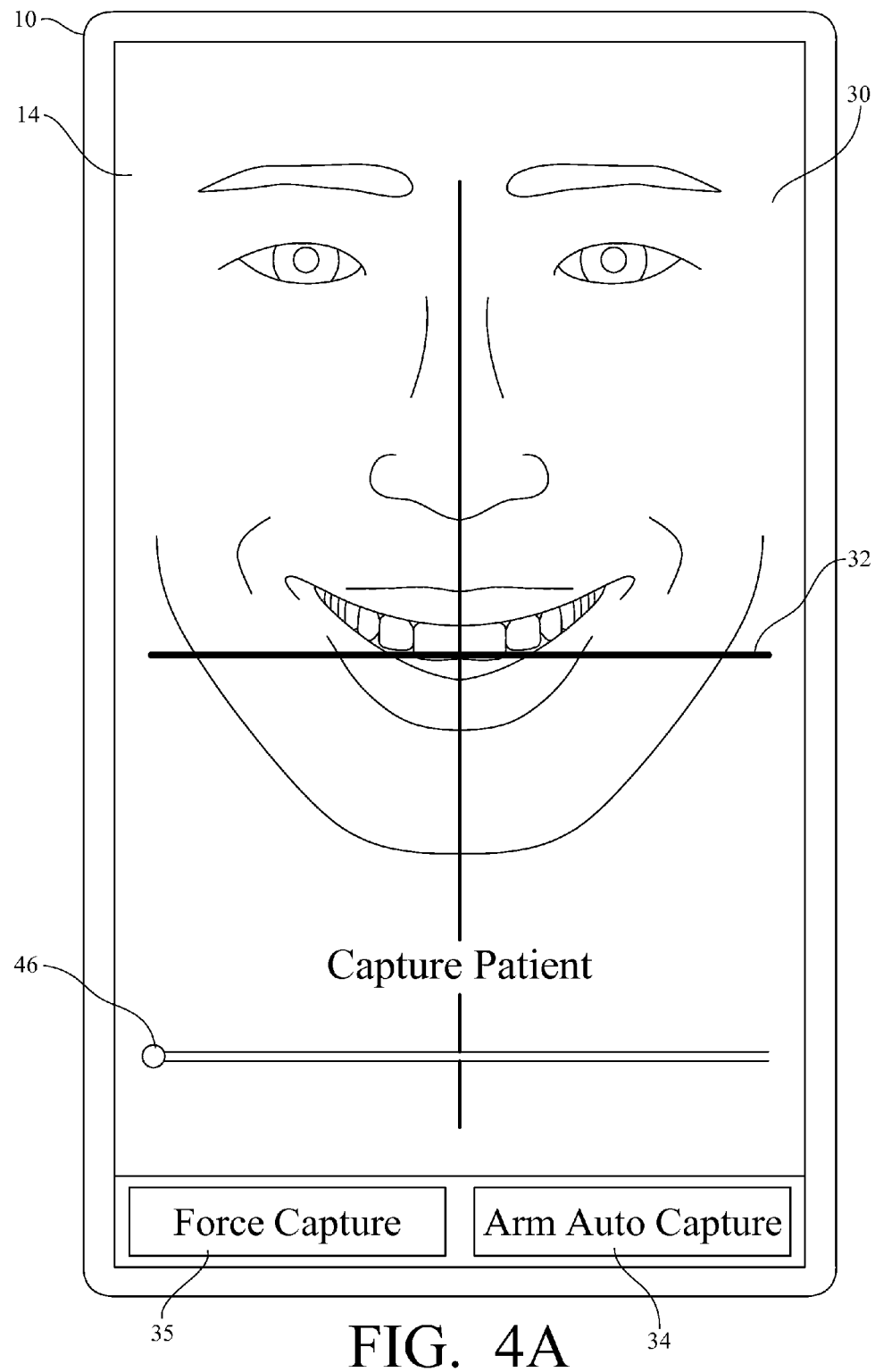
FIG. 4A is an exemplary screen shot displayed on the tablet of FIG. 1, including a real-time image of a patient.

FIG. 4A is another exemplary screen shot displayed on the screen 14 of the tablet 10 of FIG. 1. Like FIG. 1, in FIG. 4A, a real-time image 30 as captured by the camera 12 is displayed on the screen 14, along with a set of crosshairs 32.

Figure 4B:
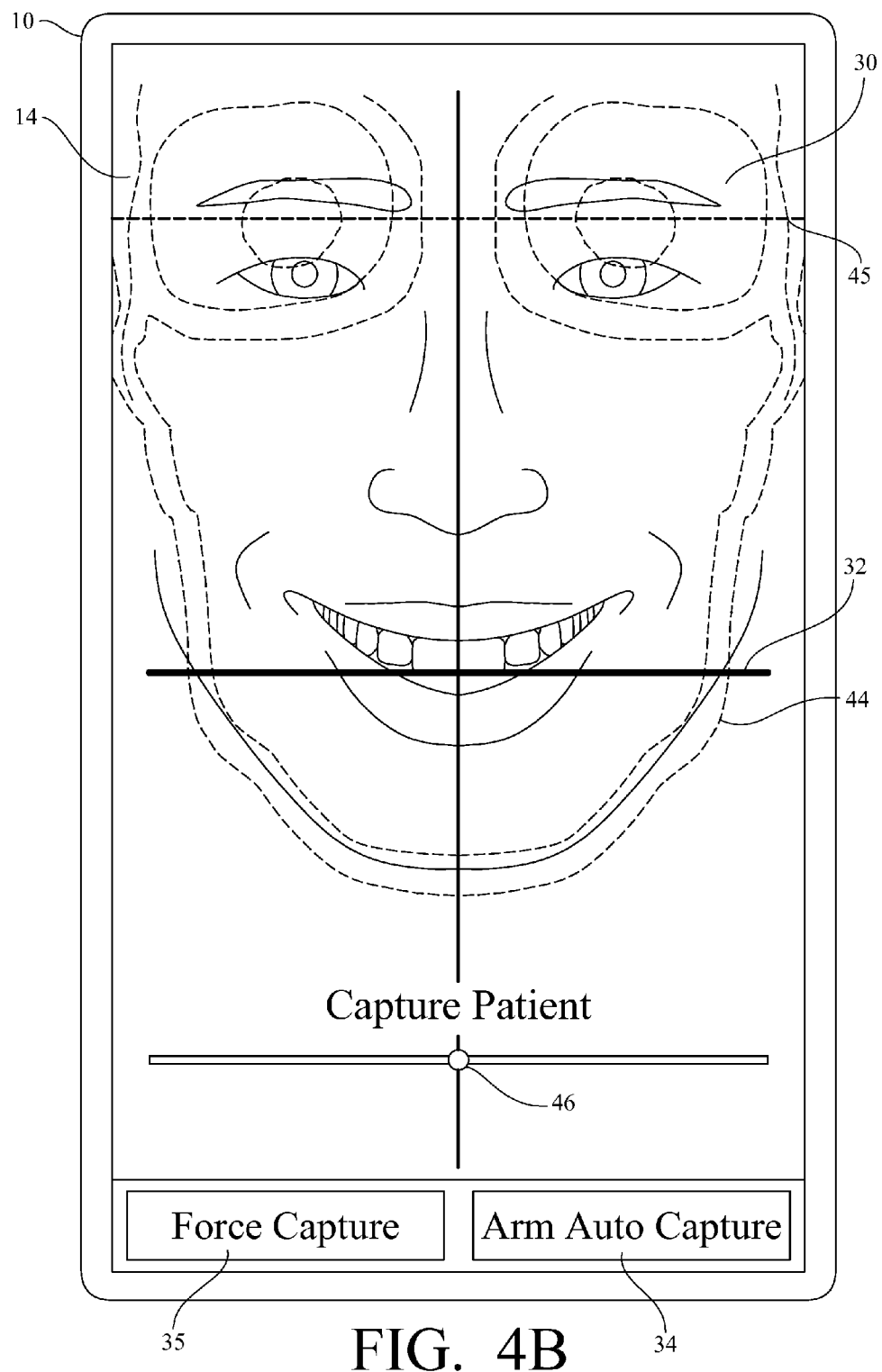
FIG. 4B is another exemplary screen shot displayed on the tablet of FIG. 1, including a real-time image of a patient along with a skull image.
Figure 4C:
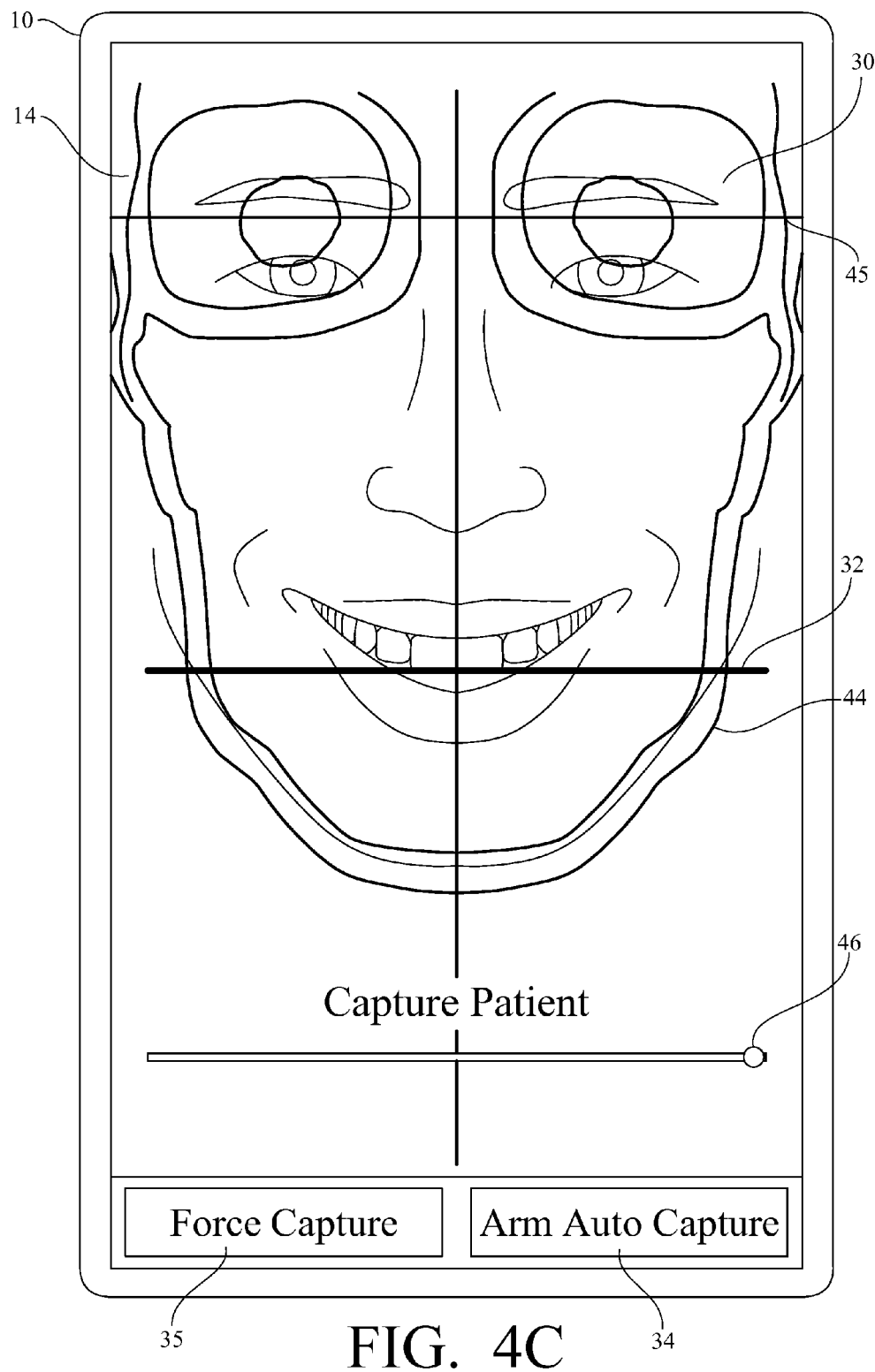
FIG. 4C is another exemplary screen shot displayed on the tablet of FIG. 1, including a real-time image of a patient along with a skull image.

Referring now to FIGS. 4B and 4C, at the commencement of the image acquisition process or sometime thereafter (either automatically or at the prompting of the operator), a skull image 44, which also serves as a facial alignment image, is retrieved from a skull image registry stored in the memory component 16 and is displayed on the screen 14, as indicated by block 108 of FIG. 2. In this example, the skull image 44 also includes a horizontal bar 45 at the midline of the eyes, which fades with the remainder of the skull image 44, as further described below. The crosshairs 32 overlay the skull image 44, such that the vertical line of the crosshairs 32 is aligned with the facial midline of the skull image 44. Furthermore, it should be recognized that the opacity of the skull image 44 can be adjusted by a slide button 46, such that the real-time image 30 can be made visible through the skull image 44. For instance, in FIG. 4B, the dashed lines for the skull image 44 indicate a lighter, more transparent image. In FIG. 4C, where the slide button 46 has been moved all the way to the right, the darker, solid lines for the skull image 44 indicate a less transparent image.

As indicated by block 110 of FIG. 2, the operator then manipulates the tablet 10 into an appropriate position and orientation to capture an image of the patient. Specifically, as shown in FIG. 1, with the patient sitting in an upright position and the patient's head level, the operator adjusts the position and orientation of the tablet 10, such that the real-time image 30 displayed on the screen 14 is a straight-on view of the patient's face, as illustrated by the viewing frame shown in FIG. 1. In other words, the tablet 10 is positioned such that the camera 12 is directly in front of the patient's face, with the camera 12 at the level of the patient's face. As shown in FIGS. 4A, 4B, and 4C, the operator also aligns the crosshairs 32 displayed on the screen 14 with the patient's front teeth, such that the incisal edge of the patient's teeth lines up with the horizontal line of the crosshairs 32, and the patient's facial midline follows the vertical line of the crosshairs 32. Furthermore, the eyes of the skull in the skull image 44 can be used by the operator to ensure that the patient is an appropriate distance away from the camera 12. For example, as shown in FIGS. 4A-4C, the eyes of the patient are below the eyes of the skull in the skull image 44, which indicates that the camera 12 should be closer to the patient. For the exemplary method of the present invention, it is not necessary to ensure the eyes of the skull in the skull image 44 are aligned with the eyes of the patient at this point; however, doing so will require less scaling of the image of the patient later, as further described below.

In order to assist the operator in properly positioning the tablet, in some implementations, the facebow app provides visual indications as to whether the tablet is in a vertical orientation. For example, although not shown in the Figures, it is contemplated that, when the tablet 10 is tilted to the left, the screen 14 displays a clockwise arrow in the top right corner of the screen 14, thus alerting the operator that the tablet 10 should be rotated clockwise. Similarly, it is contemplated that, when the tablet 10 is tilted to the right, the screen 14 again displays a counterclockwise arrow in the top left corner of the screen 14, thus alerting the operator that the tablet 10 should be rotated counterclockwise. Furthermore, it is contemplated that, when the tablet 10 is tilted either forward or backward, a red border appears around the border of the screen 14. When the tablet 10 is approaching the vertical orientation, an orange and then a yellow border appear within the red border, and when the device is held in the vertical orientation, there is a green inner border. Such colored borders and arrows thus provide a visual indication to the operator when the tablet 10 is approaching the vertical orientation.

As a further refinement, the sensitivity of the vertical alignment visual indications can be adjusted depending on the needs of the operator. For example, with a narrow tolerance, the tablet 10 must be very close to a true vertical alignment for the screen to show the green border indicating the tablet 10 is in the vertical orientation. Alternatively, with a larger tolerance, the tablet 10 may be further from a true vertical alignment for the screen to show the green border indicating the tablet 10 is in the vertical orientation.

Figure 5A:
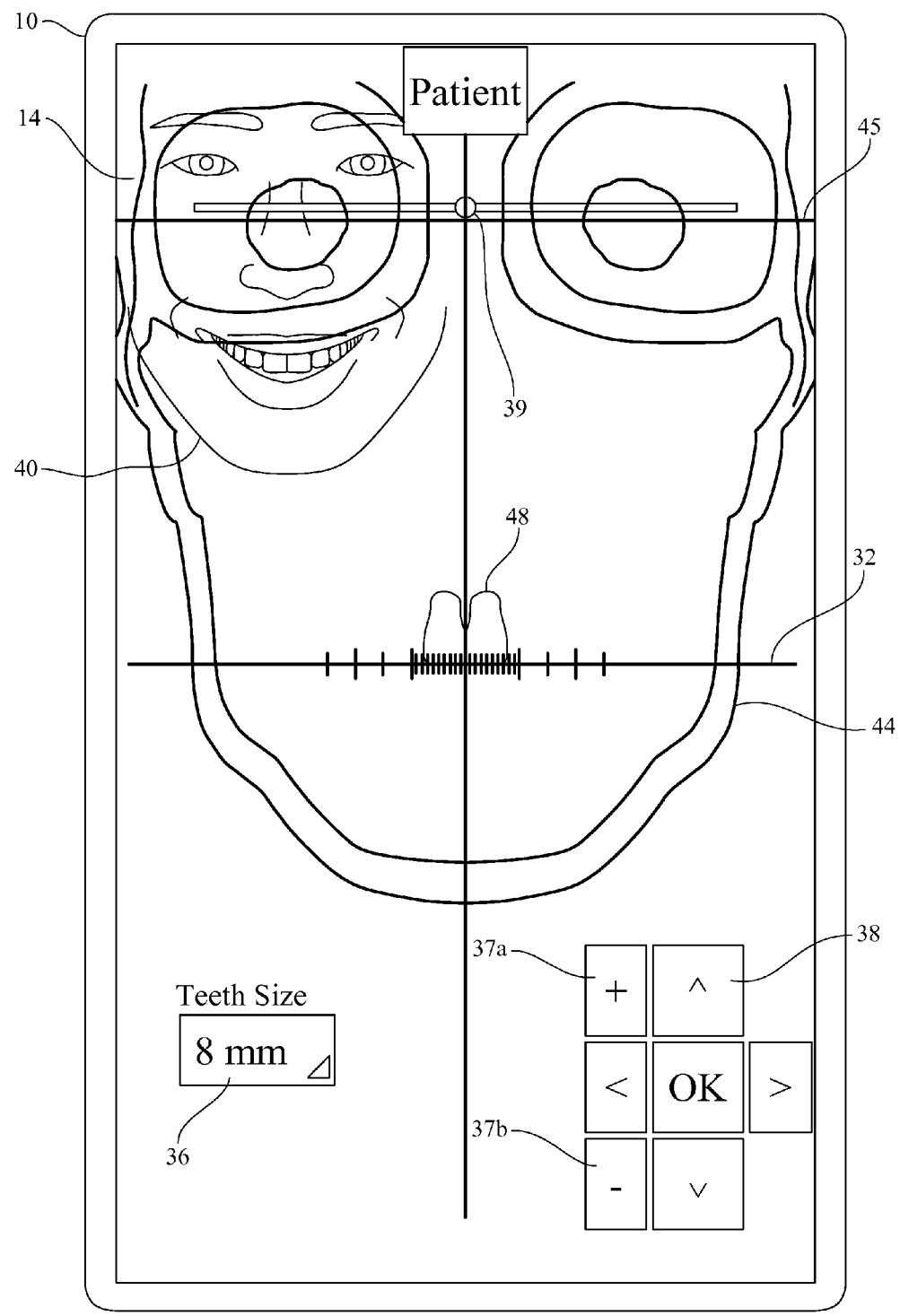
FIG. 5A is an exemplary screen shot displayed on the tablet of FIG. 1, including a captured face image of a patient overlaying a skull image.
Figure 5B:
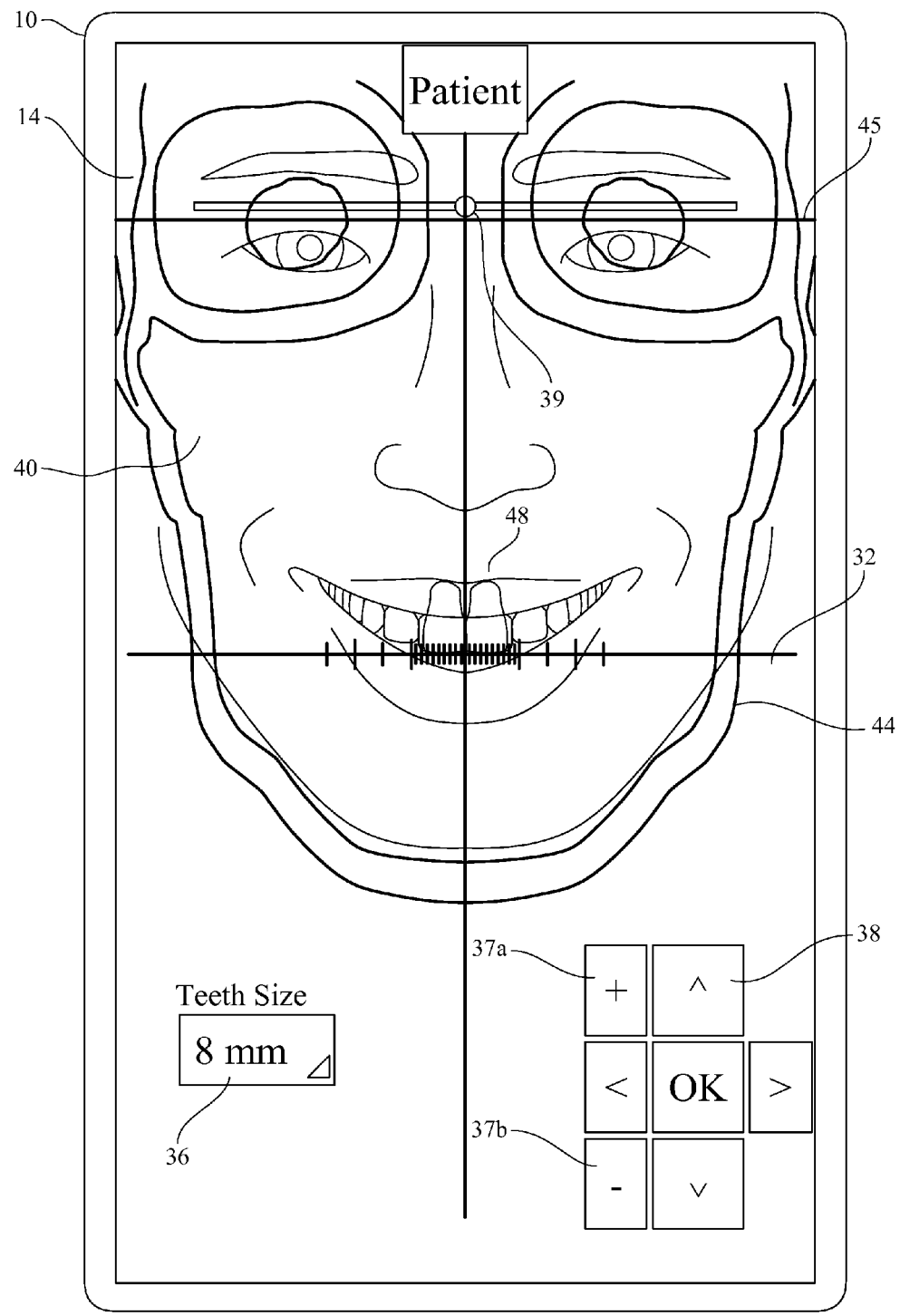
FIG. 5B is another exemplary screen shot displayed on the tablet of FIG. 1, including a captured face image of a patient overlaying a skull image.

As indicated by block 112 of FIG. 2, once the operator manipulates the tablet 10 into an appropriate position and orientation, such that the tablet 10 is in the vertical orientation and the real-time image 30 of the patient's face is properly aligned with the crosshairs 32, a photographic image of the patient's face is captured. For example, by pressing the "Arm Auto Capture" button 34 at the bottom right of the screen 14 (as shown in FIGS. 4A, 4B, and 4C), a countdown (e.g., three seconds) will begin, and subsequently, the photographic image of the patient's face is captured. In this regard, in some implementations, the "Arm Auto Capture" button 34 only works when the tablet 10 is in the vertical orientation, i.e., when the above-described green border is displayed to indicate that the tablet 10 is in the vertical orientation. Alternatively, the "Force Capture" button 35 at the bottom left of the screen 14 (as also shown in FIGS. 4A, 4B, and 4C) can be used to capture a photographic image even if the tablet 10 is not in the vertical orientation. If, after capturing the photographic image of the patient's face (i.e., a face image 40 as shown in FIGS. 5A-5B), it is determined that the patient's face is not properly aligned with the crosshairs 32, a "back" button (not shown) displayed on the tablet 10 may be used to return to the previous screen. In fact, it should be noted that, at any time, the "back" button (not shown) displayed on the tablet 10 may be used to return to a previous screen or step.

After capturing the face image 40, where the patient's face is properly aligned with the crosshairs 32, that face image 40 is stored in the memory component 16 of the tablet 10 as part of the patient file as indicated by block 114 of FIG. 2. It should be noted that, when capturing the real-time image 30 of the patient, it is preferable that as many of the patient's teeth as possible are visible, as further described below. To this end, in some embodiments, the operator can use retractors, or other similar devices, to more clearly show the patient's teeth.

After capturing and storing the face image 40, the operator now measures the size of the patient's maxillary central incisors, i.e., the two front upper teeth (or centrals). As indicated by block 120 of FIG. 2, the operator enters the measured size of the maxillary central incisors into the facebow app, and this data is stored in the memory component 16 of the tablet 10 as part of the patient file. For example, and as shown in FIGS. 5A and 5B, such data entry can be accomplished via a "Teeth Size" drop-down menu 36 displayed on the screen 14 of the tablet 10. As shown in FIGS. 5A and 5B, and as indicated by block 122 of FIG. 2, an image of two front teeth 48 (which may also be retrieved from the skull image registry described above) is also displayed on the screen 14 as part of the skull image 44 along with a series of vertical dash lines along the horizontal line of the crosshairs 32. The size of the two front teeth 48 is correlated to the size of the maxillary central incisors entered. As shown in FIGS. 5A-5B, the vertical dash lines along the horizontal line of the cross hairs 32 each represent 1 mm, such that, for example, with a maxillary central incisor size of 8 mm entered, each of the teeth in the image of two front teeth 48 are 8 mm wide (i.e., eight vertical dash lines wide).

As indicated by block 124 of FIG. 2, the operator now adjusts the face image 40 to align the face image 40 with the skull image 44, using, in part, the image of the two front teeth 48 (which are sized in accordance with the entered size of the patient's maxillary central incisors) that are displayed on the screen 14 as part of the skull image 44. Referring now to FIGS. 5A and 5B, the face image 40 is displayed on the screen 14 overlaying the skull image 44 and the crosshairs 32, and the operator can move and scale the face image 40 to align it with the skull image 44. Specifically, the operator can move the face image 40 left, right, up, and down. The operator can also scale the face image 40.

For example, as shown in FIG. 5A, the face image 40 is significantly smaller than the skull image 44, whereas, in FIG. 5B, the face image 40 and the skull in the skull image 44 are approximately equally sized, and the eyes of the patient in the face image 40 are approximately aligned with the eyes of the skull in the skull image 44. Most importantly, in FIG. 5B, the front teeth of the patient in the face image 40 are approximately aligned with the two front teeth 48 of the skull image 44.

With respect to the movement and scaling of the face image 40, in some embodiments and as shown in FIGS. 5A and 5B, certain buttons are displayed on the screen 14 of the tablet 10 to allow the operator to readily make the necessary adjustments. For example, arrow buttons (collectively indicated by reference number 38) are used to shift the face image 40 left, right, up, or down, i.e., in the direction indicated by the respective arrow. For another example, and referring still to FIGS. 5A and 5B, a + button 37a is used to enlarge the face image 40, while a − button 37b is used to shrink the face image 40. Of course, other methods well-known in the art for moving and scaling an image, such as touching the screen 14 and dragging the face image 40 into position, may be used to align the face image 40 with the skull image 44 without departing from the spirit and scope of the present invention.

As a further refinement, to assist the operator in properly aligning the face image 40 with the skull image 44, in some embodiments and as shown in FIGS. 5A and 5B, a slide button 39 is displayed on the screen 14 of the tablet 10, in the top center portion of the screen 14. This slide button 39 works in a similar manner as the slide button 46 described above with respect to FIGS. 4A-4C, but, in this case, adjusts the opacity of the face image 40. When the slide button 39 is in the center of the screen 14, the face image 40 and the skull image 44 are similarly visible. Although not shown, when the slide button 39 is moved to the right, the face image 40 becomes less transparent, such that the face is more visible. When the slide button 39 is moved to the left, the face image 40 becomes more transparent, such that the skull image 44 is more visible. In this way, the operator can adjust the opacity of the face image 40 in order to better see the various features of the patient's face and/or the skull as necessary for proper alignment of the face image 40 with the skull image 44.

As should be clear from the foregoing description, scaling the face image 40 to match the skull image 44 allows the system and methods of the present invention to be used regardless of the patient's actual facial dimensions.

Once the face image 40 is properly aligned with the skull image 44, a composite image is captured and stored in the memory component 16 of the tablet 10 as part of the patient file, as indicated by blocks 126, 128 of FIG. 2.

Figure 6:
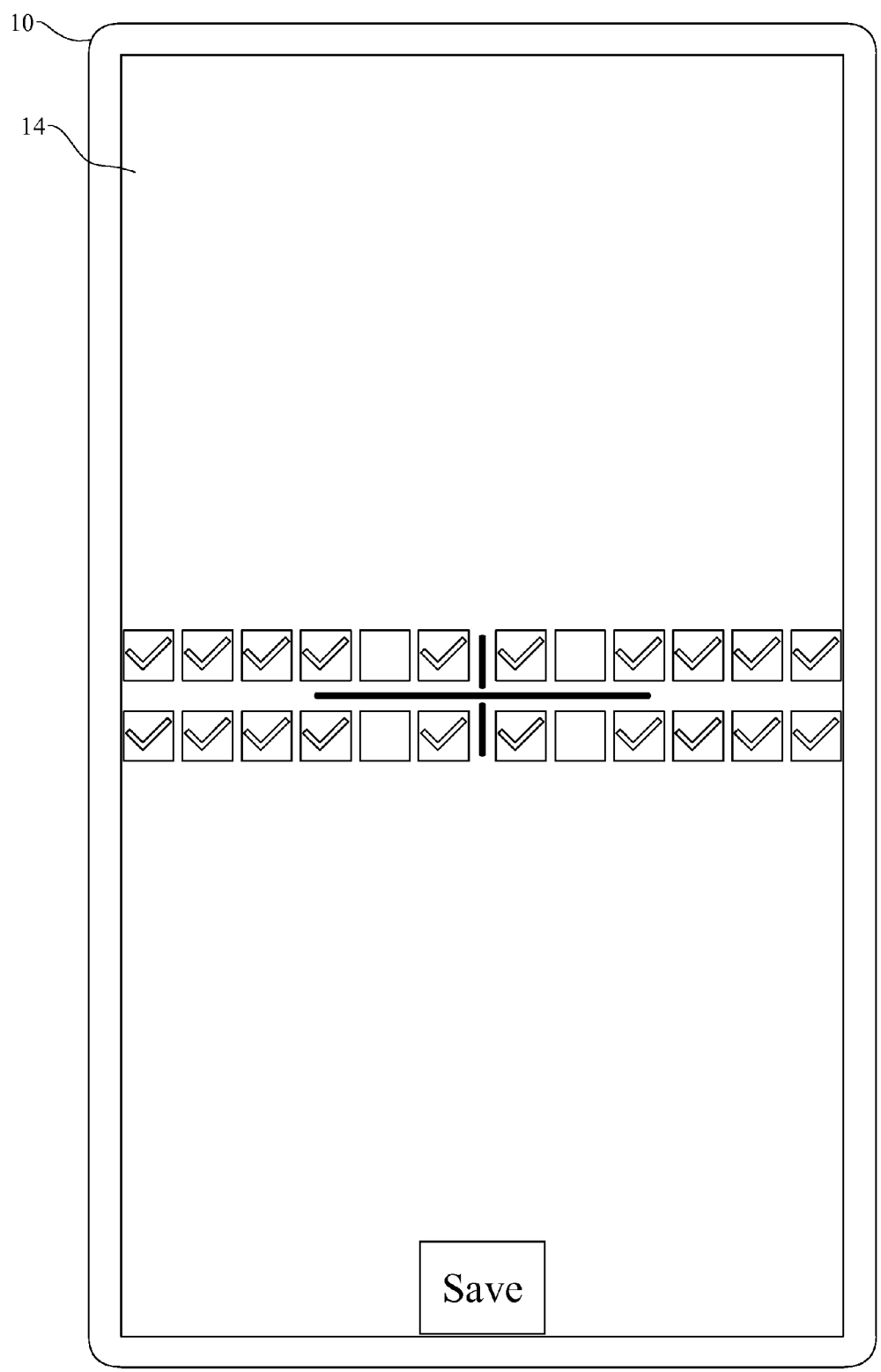
FIG. 6 is an exemplary screen shot displayed on the tablet of FIG. 1, including a tooth chart for recording which of a patient's maxillary (upper) teeth touch which of a patient's mandibular (lower) teeth.

Now, as indicated by block 130 of FIG. 2, a tooth chart is displayed on the screen 14 of the tablet 10, which includes two rows of boxes representative of the teeth of the patient. The operator visually inspects the patient's teeth and records which of the patient's maxillary (upper) teeth touch which of the patient's mandibular (lower) teeth. In some embodiments, and as shown in FIG. 6, this can be accomplished by having the operator "check" the appropriate boxes in the two rows as the operator completes such a visual inspections. The identification of the "touching" teeth is also stored in the memory component 16 of the tablet 10 as part of the patient file, as indicated by block 132 of FIG. 2. The resultant tooth chart can be later used to confirm the position of a maxillary cast and mandibular cast, as further described below.

All of the collected information and data is now stored in the memory component 16 of the tablet 10 in the patient file. Specifically, the patient file includes all pertinent characteristics of the occlusal arch. The patient's midline and cant have been captured in relation to the crosshairs in the face image 40. Furthermore, the face image 40 can be used to determine the steepness of the occlusal arch (i.e., the anterior posterior relationship), as further described below.

Replicating Patient Alignment

The patient file, which contains all of the collected information and data, may be sent to or retrieved by a third party. Such collected information and data can then be used to replicate the alignment of the patient's occlusal arch with a maxillary cast in an articulator for the production of customized dental prosthetics for the patient. Advantageously, the patient file containing the characteristics of the occlusal arch of the patient may be sent to a third party for use on a different tablet or other portable computing device which has the facebow app. However, the same tablet 10 used for the steps described above may also be used in the production of customized dental prosthetics for the patient. In either event, a tablet or other portable computing device with the virtual facebow app installed is used to carry out the following steps.

Figure 7A:
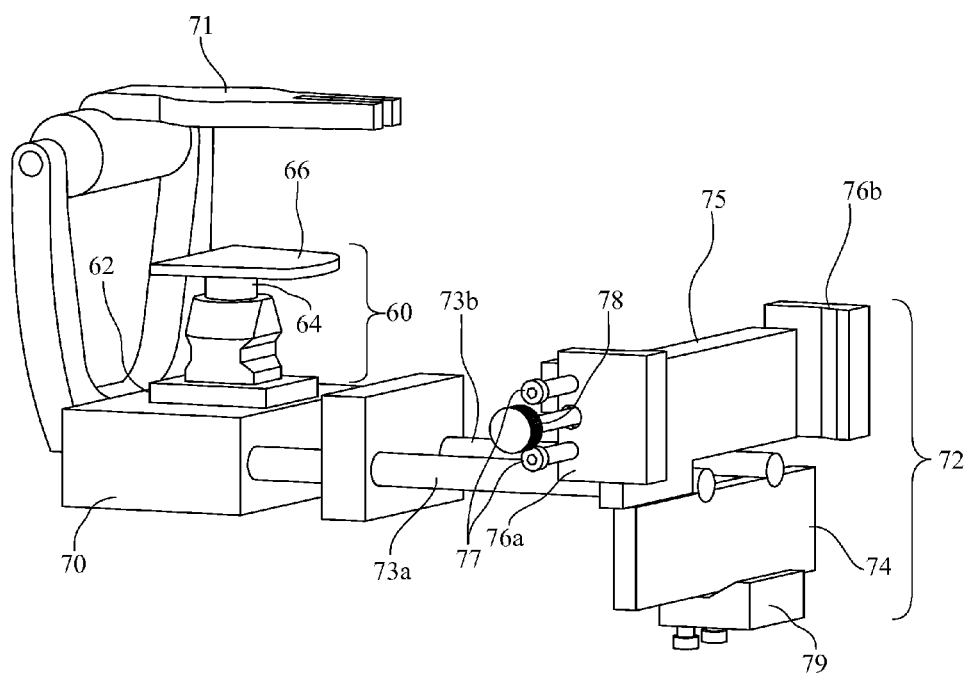
FIG. 7A is a perspective view of an articular with a universal occlusal stand and a mounting platform attached for receiving and positioning the tablet relative to the universal occlusal stand.
Figure 7B:
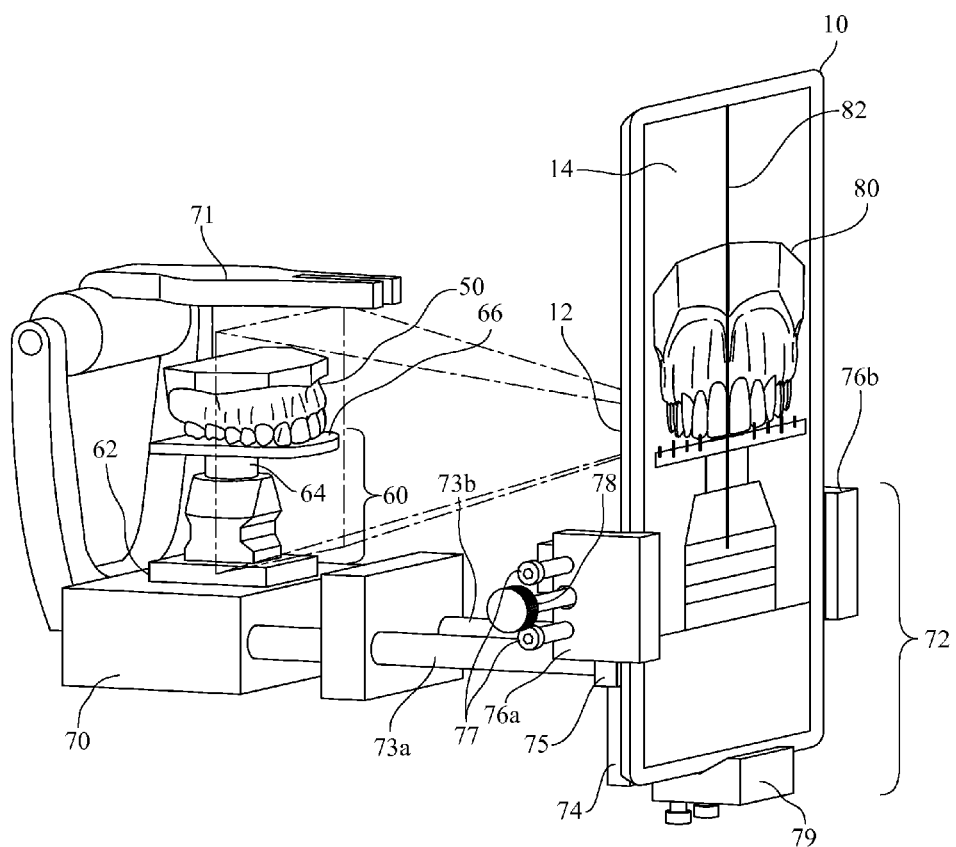
FIG. 7B is a perspective view of the articular with the universal occlusal stand and the mounting platform of FIG. 7A with a maxillary cast affixed to the universal occlusal stand and the tablet affixed to the attached mounting platform.

Referring now to FIG. 7B, a maxillary cast 50 for the patient is created by methods well-known in the art, for example, by first forming an impression mold, and then filling the cavity of the impression mold with an appropriate compound. Irrespective of how the maxillary cast 50 is created, it is placed on a universal occlusal stand 60, which is designed to position the maxillary cast 50 relative to the camera 12 of the tablet 10 with the facebow app, as further described below.

Referring now to FIG. 7A, the universal occlusal stand 60 includes a base 62, a post 64 that extends upwardly from the base 62, and an adjustable plate 66 mounted to the post 64. As is well-known in the art, the adjustable plate 66 is mounted such that it can rotate a predetermined distance (for example, about 20°) in any direction relative to the post 64. In short, the adjustable plate 66 is effectively mounted such that the occlusal plane of the maxillary cast 50 can readily be adjusted relative to the base 62. Furthermore, although not shown in the Figures, as is also well-known in the art, the universal occlusal stand 60 may also include a means for adjusting the height of the adjustable plate 66 relative to the base 62 of the universal occlusal stand 60, for example, by allowing the post 64 to be raised and lowered relative to the base 62. Thus, the maxillary cast 50 can be raised and lowered relative to the base 62 of the universal occlusal stand 60.

Referring still to FIG. 7A, the universal occlusal stand 60 is positioned on top of and secured to a mounting platform 70 of a lab stand. The lab stand further includes an upper member 71 which is rotatable relative to the mounting platform 70 such that the upper member 71 can be positioned directly above the universal occlusal stand 60, as further described below. Extending from the front of this mounting platform 70 is a clamp assembly 72, which holds the tablet 10, and thus the camera 12 of the tablet 10, in a fixed position relative to the universal occlusal stand 60. In this exemplary embodiment, and as shown in FIG. 7A, the clamp assembly 72 includes two rods 73a, 73b that extend from the front of the mounting platform 70. A lower support bar 74 is then secured to these rods 73a, 73b by screws or similar fasteners. An upper support bar 75 is then secured to the lower support bar 74 by screws or similar fasteners. A clamping member 76a, 76b is mounted to each end of the upper support bar 75. In so mounting each clamping member 76a, 76b to the upper support bar 75, a combination of spring-loaded shoulder screws 77 and an adjustment screw 78 is preferably used to allow for fine adjustments of the position of each clamping member 76a, 76b relative to the upper support bar 75, so that the clamping members 76a, 76b may be moved into engagement with the lateral edges of the tablet 10 (as shown in FIG. 7B). Similarly, a third clamping member 79 is mounted to the lower support bar 74 to engage and support the lower edge of the tablet 10 (as also shown in FIG. 7B). Of course, it should be understood that an image capture device independent of the tablet 10 may be held in a fixed position relative to the universal occlusal stand 60, wherein the screen 14 of the tablet 10 displays the real-time image captured by the image capture device.

Figure 8:
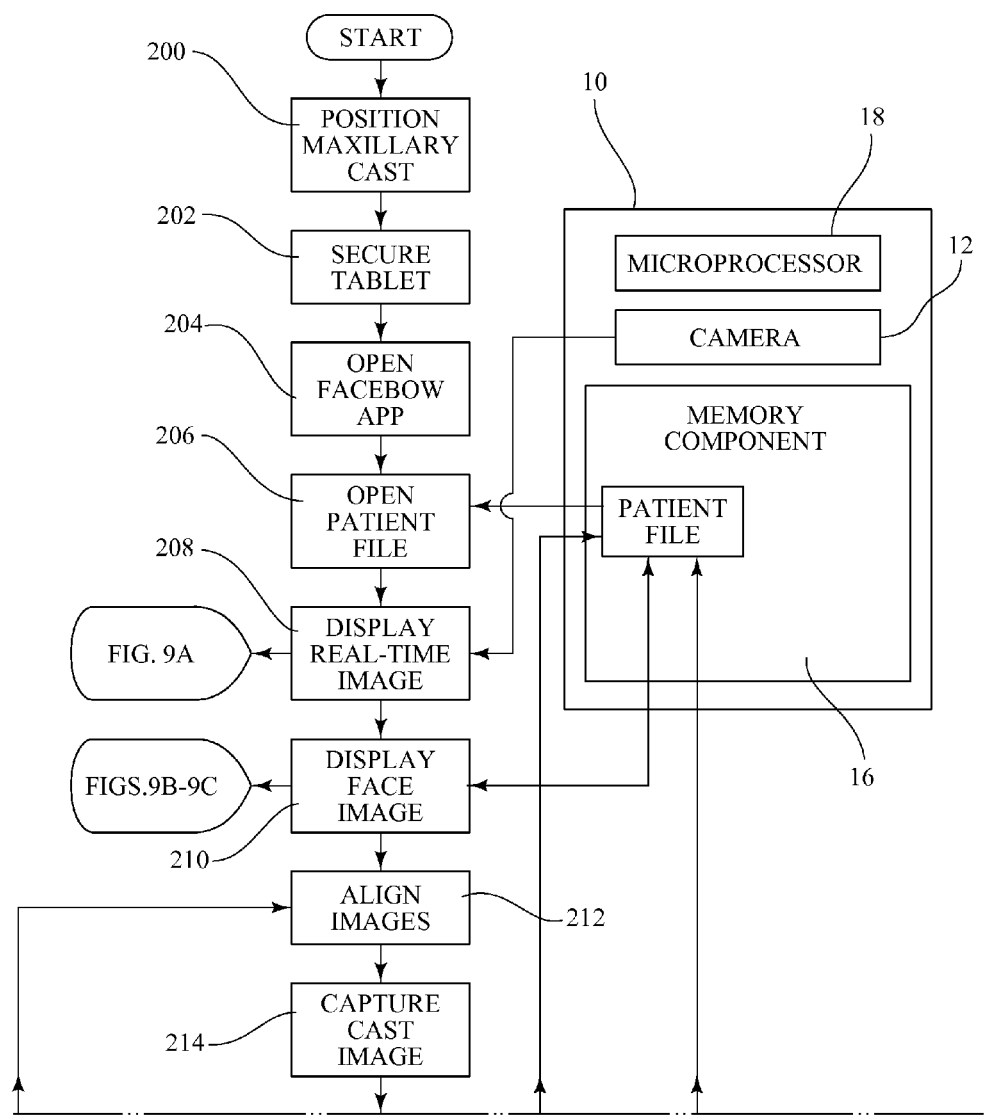
FIG. 8 is a flow chart of an exemplary implementation of the method of the present invention, illustrating the exemplary steps of replicating patient alignment and producing customized dental prosthetics for the patient.
Figure 8A:
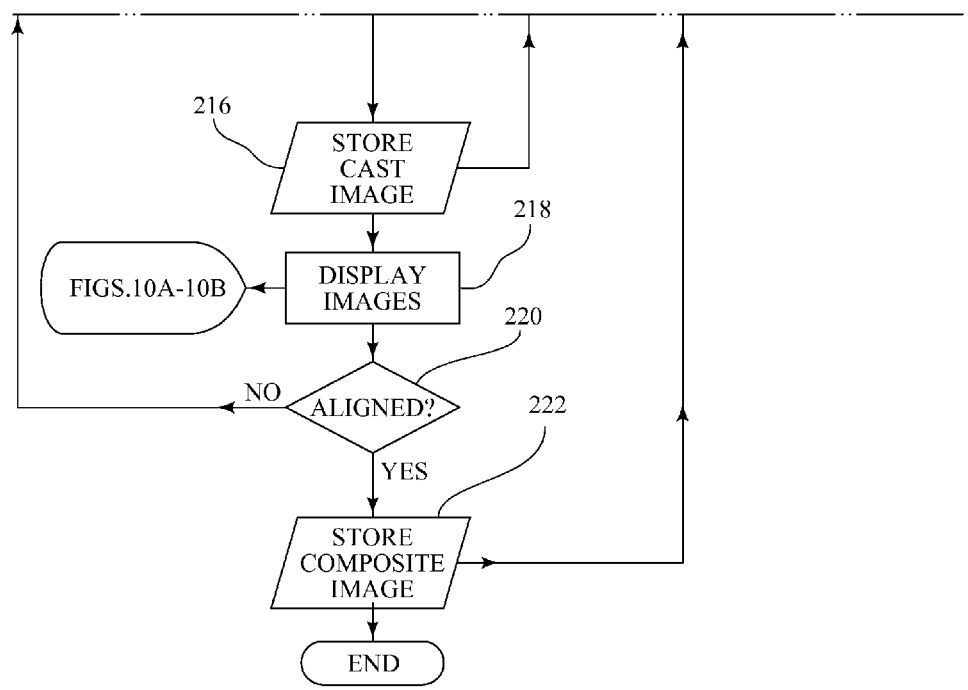
FIG. 8A is a continuation of the flow chart of FIG. 8.

Referring now to the flow chart of FIG. 8 (which also includes the continuation in FIG. 8A in the description that follows), the maxillary cast 50 is placed on the adjustable plate 66 of the universal occlusal stand 60, as indicated by block 200 of FIG. 8. If necessary, the maxillary cast 50 may also be temporarily affixed to the adjustable plate 66 by means well-known in the art (for example, using putty) in order to stabilize the maxillary cast 50. As is also well-known in the art, although not shown, it is contemplated that the adjustable plate 66 of the universal occlusal stand 60 could also include a front stop, which is used to ensure the front teeth of the maxillary cast 50 are correctly positioned relative to the universal occlusal stand 60. The tablet 10 (which may be the same one described above with respect to FIG. 1 or another tablet or other portable computing device with the facebow app) is secured relative to the universal occlusal stand via the clamp assembly 72, as indicated by block 202 of FIG. 2.

After placing the maxillary cast 50 on the adjustable plate 66 of the universal occlusal stand 60 and securing the tablet 10 relative to the universal occlusal stand via the clamp assembly 72, an operator, such as a doctor, nurse, or technician, opens the virtual facebow app on the tablet 10, as indicated by block 204 of FIG. 8. In other words, the operator initiates the app, which again causes computer-readable instructions stored in a memory component 16 of the tablet 10 to be executed by a microprocessor 18. Such computer-readable instructions can be coded into a computer-readable form using standard programming techniques and languages, and with benefit of the following description, such programming is readily accomplished by one of ordinary skill in the art.

As indicated by block 206 of FIG. 8, the operator then opens an existing patient file. Referring once again generally to FIG. 3, the operator would then select the "Lab" button (or similar button) of the patient file (e.g., the John Doe file shown in FIG. 3) to proceed with the mounting of the maxillary cast 50.

Figure 9A:
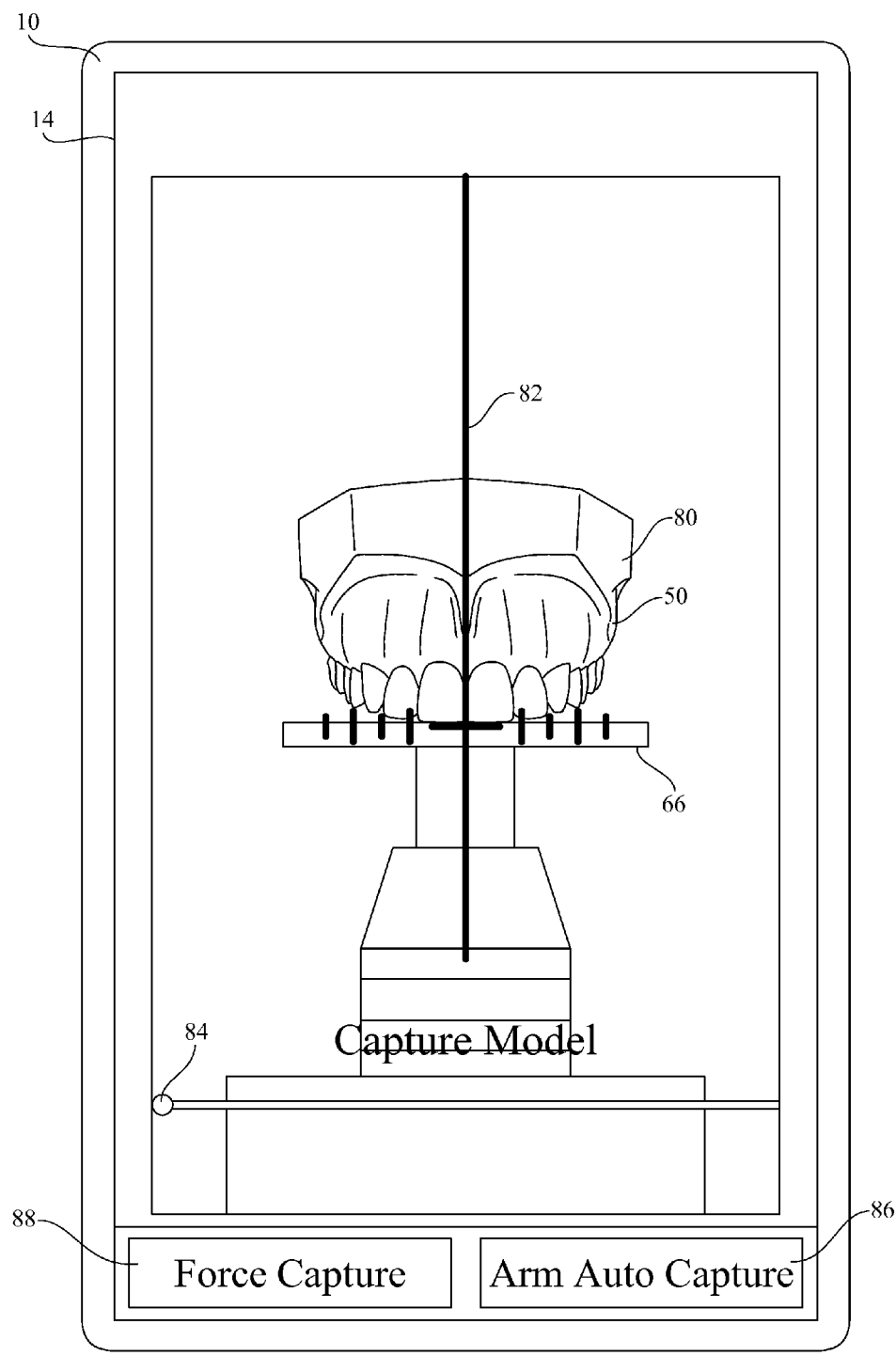
FIG. 9A is an exemplary screen shot displayed on the tablet of FIG. 7B, including a real-time image of the maxillary cast affixed to the universal occlusal stand of FIG. 7B.

As indicated by block 208 of FIG. 8, after opening the patient file, a real-time image 80 of the maxillary cast 50 on the universal occlusal stand 60 as captured by the camera 12 is displayed on the screen 14, along with a set of crosshairs 82 (i.e., a vertical line and a horizontal line which intersect at a central position on the screen 14 along with a series of vertical dash lines along the horizontal line). Such a real-time image 80 and a set of crosshairs 82 is shown in FIG. 9A.

Figure 9B:
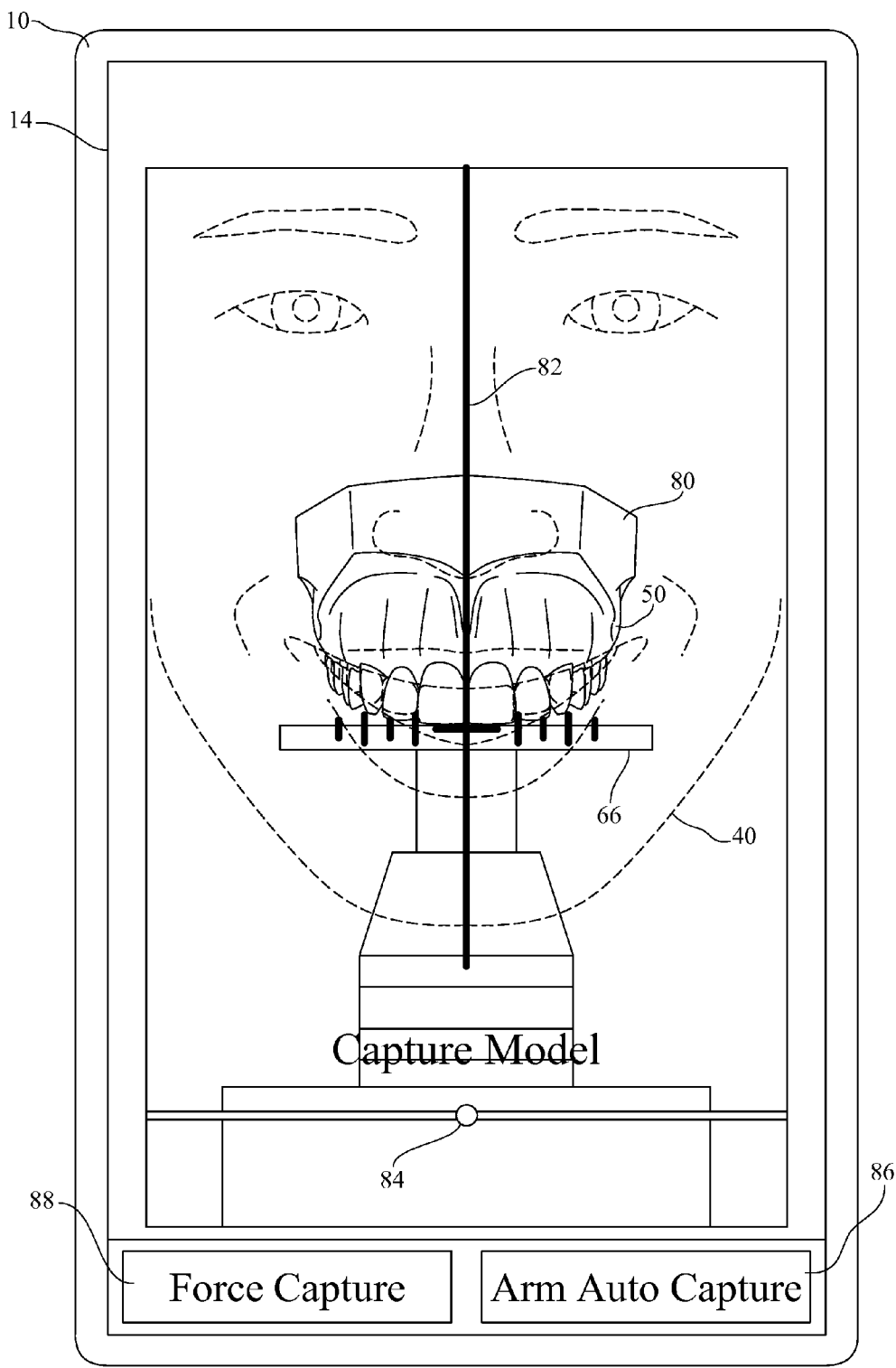
FIG. 9B is another exemplary screen shot displayed on the tablet of FIG. 7B, including a real-time image of the maxillary cast affixed to the universal occlusal stand of FIG. 7B, along with a captured face image of the patient.
Figure 9C:
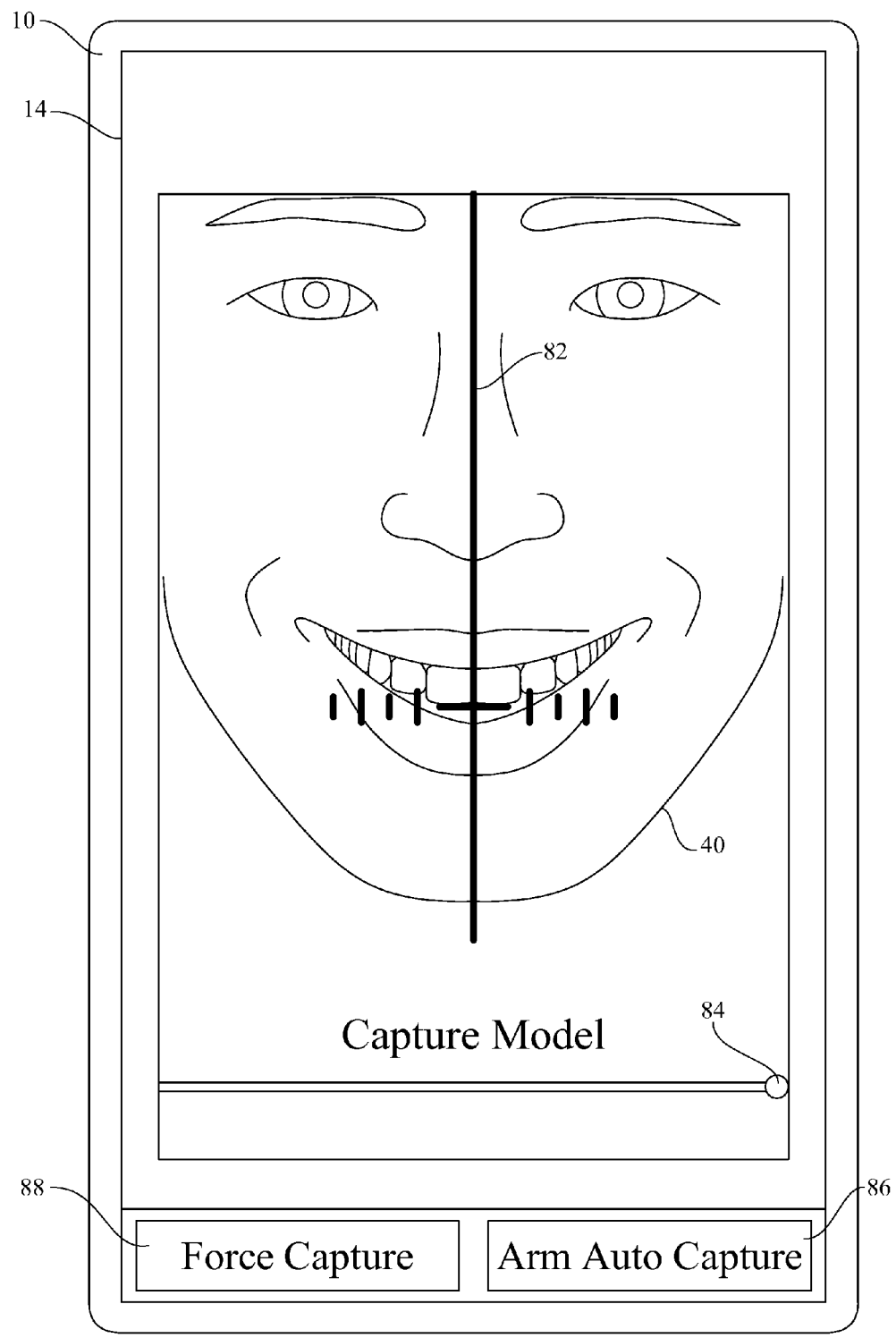
FIG. 9C is another exemplary screen shot displayed on the tablet of FIG. 7B, including the captured face image of the patient.

Referring now to FIGS. 9B and 9C, the face image 40, as retrieved from the patient file stored in the memory component 16 of the tablet 10 is then also displayed, as indicated by block 210 of FIG. 8. The real-time image 80 captured by the camera 12 and crosshairs 82 overlay the face image 40, such that the horizontal line of the crosshairs 82 is aligned with the incisal edge of the teeth of the face image 40, and the vertical line of the crosshairs 82 is aligned with the facial midline of the face image 40, reflecting the alignment of the face image 40 with the crosshairs 32 previously achieved and described above with respect to blocks 124, 126, 128 of FIG. 2. Furthermore, it should be recognized that the opacity of the face image 40 can be adjusted by a slide button 84, such that the real-time image 80 is visible through the face image 40. For instance, in FIG. 9B, the dashed lines for the face image 40 indicate a lighter, more transparent image. In FIG. 9C, where the slide button 84 has been moved all the way to the right, the solid lines for the face image 40 indicate a less transparent image.

As indicated by block 212 of FIG. 8, the maxillary cast 50 is then positioned to align the real-time image 80 of the maxillary cast 50 with the face image 40 and crosshairs 82 displayed on the screen 14. Specifically, the operator adjusts the plate 66 of the universal occlusal stand 60 until the real-time image 80 of the teeth of the maxillary cast 50 is aligned with the patient's teeth as shown in the face image 40. As described above, the universal occlusal stand 60 allows the maxillary cast 50 to be raised or lowered, as well as adjustment of the occlusal plane through manipulation of the adjustable plate 66 of the universal occlusal stand 60.

Furthermore, as the face image 40 was previously aligned with the crosshairs 32, when the maxillary cast 50 is properly aligned, the front teeth of the maxillary cast 50 are also aligned with the crosshairs 82 displayed on the screen 14, such that the incisal edges of the front teeth of the maxillary cast 50 line up with the horizontal line, and the midline of the maxillary cast 50 follows the vertical line. The vertical dashed lines positioned adjacent to the horizontal line of the crosshairs 82 also provide additional visual indicators to assist in the alignment of the real-time image 80 of the maxillary cast 50 with the face image 40.

Figure 10A:
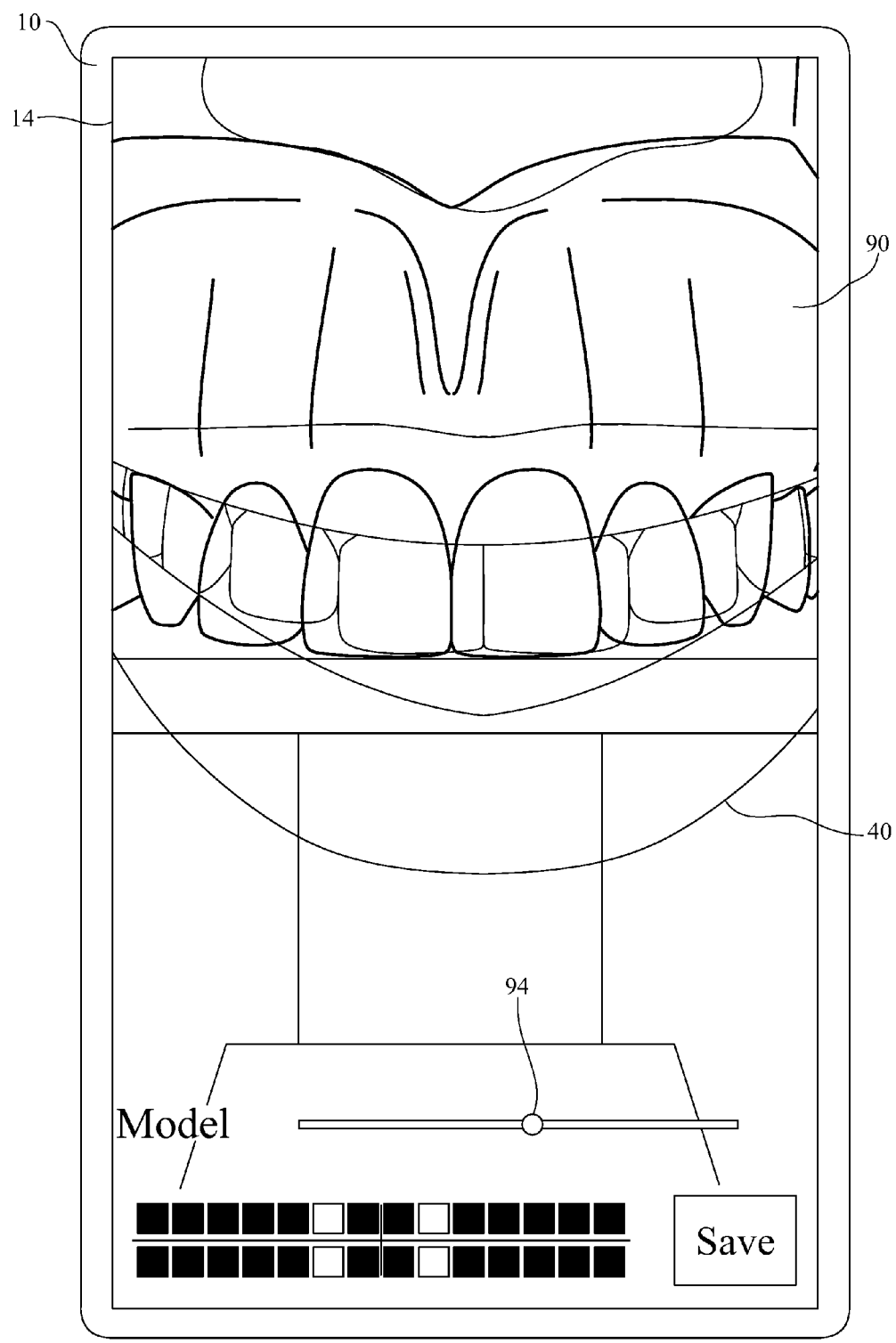
FIG. 10A is an exemplary screen shot displayed on the tablet of FIG. 7B, including both the cast image and the face image to review and verify proper alignment.
Figure 10B:
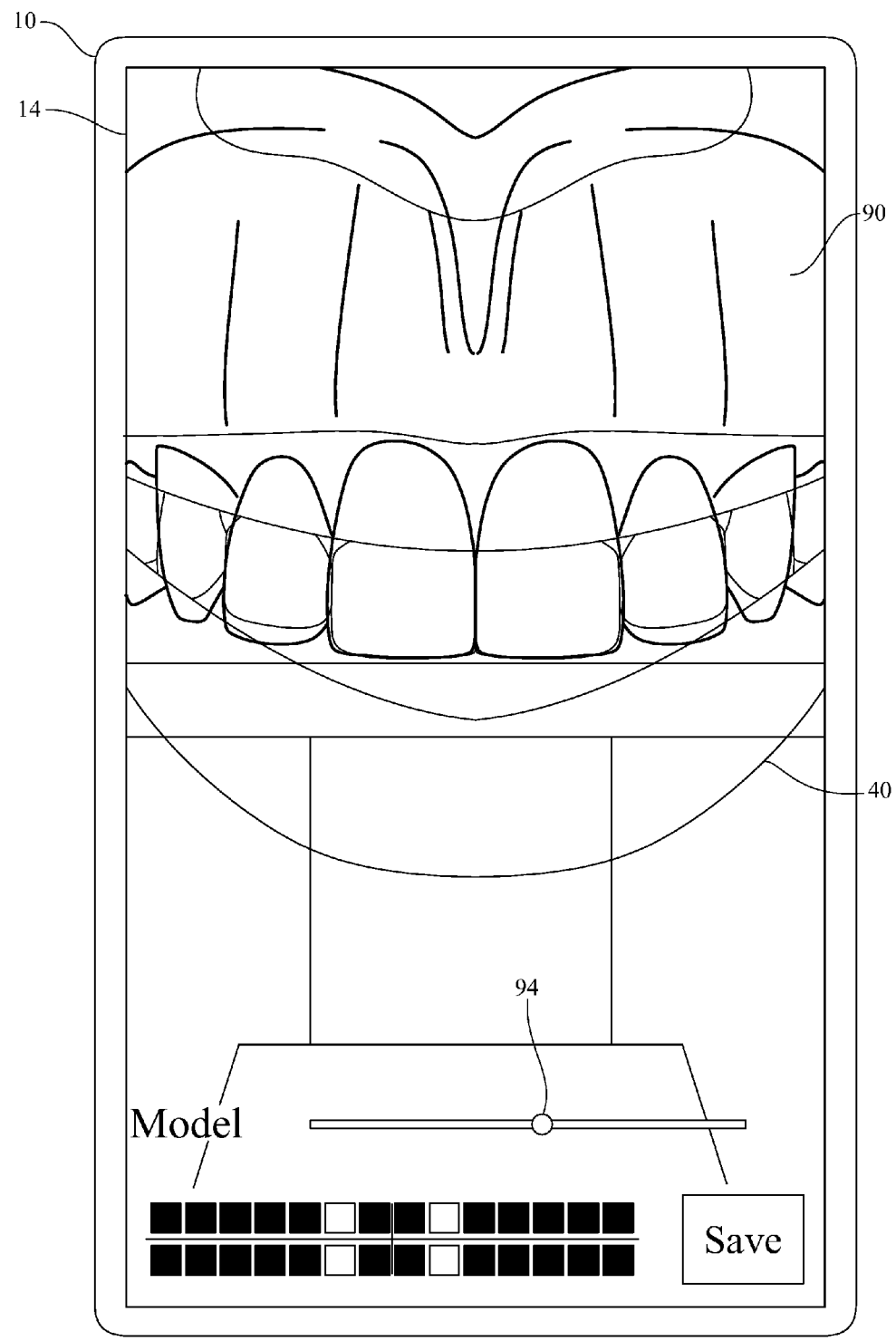
FIG. 10B is another exemplary screen shot displayed on the tablet of FIG. 7B, including both the cast image and the face image to review and verify proper alignment.

As indicated by block 214 of FIG. 8, once the real-time image 80 of the maxillary cast 50 is substantially aligned with the face image 40 and the crosshairs 82, a photographic image of the maxillary cast 50 (i.e., a cast image 90 as shown in FIGS. 10A-10B) is captured. For example, by pressing the "Arm Auto Capture" button 86 at the bottom right of the screen 14 (as shown in FIGS. 9A and 9B), a countdown (e.g., three seconds) will begin, and subsequently, a cast image 90 is captured. In this regard, in some implementations and as described above with respect to FIGS. 4A-4C, the "Arm Auto Capture" button 86 only works when the tablet 10 is in the vertical orientation, i.e., when a green border is displayed to indicate that the tablet 10 is in the vertical orientation. Alternatively, the "Force Capture" button 88 at the bottom left of the screen 14 can be used to capture a photographic image even if the tablet 10 is not in the vertical orientation.

After capturing the cast image 90, where the maxillary cast 50 is properly aligned with the crosshairs 82, the cast image 90 is stored in the memory component 16 of the tablet 10 as part of the patient file as indicated by block 216 of FIG. 8.

As indicated by block 218 and decision 220 of FIG. 8, after capturing the cast image 90, the alignment of the cast image 90 to the face image 40 is verified.

Referring now to FIGS. 10A and 10B, in order to assist the operator in verifying the alignment of the maxillary cast 50, the screen 14 of the tablet 10 displays the cast image 90 set in position relative to the overlaying face image 40 without any crosshairs. The operator is now able to zoom in on the overlaying images to ensure the teeth of the maxillary cast 50 are properly aligned with the teeth on the face image 40. If they are not properly aligned (as shown in FIG. 10A), the operator returns to the previous screen, by pressing a "back" button (not shown) displayed on the tablet 10 and repeats steps 212 and 214 until proper alignment (as shown in FIG. 10B) is achieved and verified.

Furthermore, it should be recognized that the opacity of the face image 40 and the cast image 90 can be adjusted by a slide button 94, such that the face image 40 and the cast image 90 can be individually or simultaneously visible. This slide button 94 works in a similar manner as the slide buttons 39, 46, and 83 described above with respect to FIGS. 4A-4C, 5A-5B, and 9A-9C, but, in this case, adjusts the opacity of both the face image 40 and the cast image 90. When the slide button 94 is in the center of the screen 14, the face image 40 and the cast image 90 are similarly visible. Although not shown, when the slide button 94 is moved to the right, the cast image 90 becomes less transparent, such that the maxillary cast 50 is more visible. When the slide button 94 is moved to the left, the face image 40 becomes less transparent, such that the face is more visible. In this way, the operator can adjust the opacity of the face image 40 and/or the cast image 90 in order to better verify proper alignment of the cast image 90 to the face image 40.

Once proper alignment is achieved and verified, a composite image of the cast image 90 and the face image 40 is also captured and stored in the memory component 16 of the tablet 10 as part of the patient file, as indicated by block 222 of FIG. 8. As shown in FIGS. 10A-10B, in the lower portion of the screen 14 the composite image also includes a replica of the patient's tooth chart, as described above with respect to blocks 130 and 132.

Referring again to FIG. 8, once the maxillary cast 50 is properly aligned with the face image 40, such that all of the visible teeth in the face image 40 are in alignment with the corresponding teeth of the maxillary cast 50, the steepness of the patient's occlusal arch is also accurately replicated by the angle of the maxillary cast 50. As described above, it is preferable that, when initially capturing the real-time image 30 of the patient, that as many of the patient's teeth as possible are visible. This allows alignment not only of the front teeth of the patient, but ideally of the molars of the patient as well, which will result is a more accurate replication of the patient's occlusal arch.

At least five image files are now stored in the memory component 16 of the tablet 10 as part of the patient file, along with other patient information, including: (i) a photographic image of the patient's face (i.e., the face image 40); (ii) a composite image of the face image 40 and the skull image 44; (iii) the tooth chart; (iv) a photographic image of the maxillary cast 50 (i.e., the cast image 90); and (v) a composite image of the cast image 90 and the face image 40. It should be noted that, in capturing the above images, the opacity of the components of each image are permanently set by the placement of the respective slide button when the image is captured. These five image files can be permanently stored as part of a medical record and/or sent to a third party, such as a dentist or orthodontist, for use in future dental care for the patient.

For example, although not shown in the Figures, in a process well-known in the art, the operator attaches a mounting plate (not shown) to the underside of the upper member 71. The mounting plate that is used is dependent on the articulator that will be subsequently used to fix and record the positions of the maxillary cast 50 to a mandibular cast for the lower teeth. In any event, plaster or a similar mounting material is applied to the bottom of the mounting plate and/or the upper surface of the maxillary cast, and the upper member 71 is rotated downward until an incisal pin (not shown) ensures that the upper member 71 is flat, and the mounting material is allowed to set so that the maxillary cast 50 is fixed to the mounting plate.

After the maxillary cast 50 is fixed to the mounting plate, the maxillary cast 50 and a mandibular cast (not shown), can then be mounted to an articulator by means well-known in the art. Once the maxillary cast 50 and the mandibular cast are mounted to the articulator, the maxillary cast 50 and the mandibular cast are used to simulate the bite of the patient. The operator can now compare the fit of the maxillary cast 50 and the mandibular cast. To this end, the operator verifies that the same teeth on the maxillary cast 50 are touching the same teeth of the mandibular cast as the patient's actual teeth recorded on the tooth chart, as described above with respect to blocks 130, 132 of FIG. 2. If there is a discrepancy between the casts and the tooth chart, either the maxillary or mandibular casts are remounted in order to ensure that the casts in the articulator are an accurate recreation of the patient's actual teeth.

One of ordinary skill in the art will recognize that additional embodiments and implementations are also possible without departing from the teachings of the present invention. This detailed description, and particularly the specific details of the exemplary embodiments and implementations disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:

1. A method for recording characteristics of the occlusal arch of a patient using a portable computing device, comprising the steps of:
    upon receiving an instruction from an operator, creating a patient file for the patient and storing the patient file in a memory component of the portable computing device;
    upon receiving an instruction from the operator, using an image capture device of the portable computing device to capture an image of the patient, including the teeth of the patient;
    displaying the image of the patient on a screen of the portable computing device;
    retrieving a facial alignment image stored in the memory component of the portable computing device, wherein the facial alignment image includes a set of crosshairs;
    displaying the facial alignment image overlaying the image of the patient on the screen;
    aligning the set of crosshairs of the facial alignment image with the front teeth of the patient on the image of the patient; and
    upon receiving an instruction from the operator, capturing a face image of the patient, and storing the face image in the memory component of the portable computing device as part of the patient file.

2. The method as recited in claim 1, wherein the facial alignment image is a skull image.

3. The method as recited in claim 2, wherein the step of aligning the facial alignment image with the image of the patient further comprises aligning eyes of the skull image with eyes of the patient.

4. The method as cited in claim 1, wherein the set of crosshairs of the facial alignment image has a horizontal line and a vertical line.

5. The method as recited in claim 4, wherein alignment of the facial alignment image comprises aligning the vertical line of the set of crosshairs with a facial midline of the patient and aligning the horizontal line of the set of crosshairs with an incisal edge of the front teeth of the patient.

6. The method as recited in claim 1, and further comprising the step of:
    upon receiving an instruction from the operator, adjusting the opacity of the facial alignment image as displayed on the screen of the portable computing device.

7. A method for recording characteristics of the occlusal arch of a patient using a portable computing device, comprising the steps of:
    upon receiving an instruction from an operator, creating a patient file for the patient and storing the patient file in a memory component of the portable computing device;
    upon receiving an instruction from the operator, using an image capture device of the portable computing device to capture an image of the patient, including the teeth of the patient;
    displaying the image of the patient on a screen of the portable computing device;
    retrieving a skull image stored in the memory component of the portable computing device;
    displaying the skull image overlaying the image of the patient on the screen;
    aligning the skull image with the image of the patient;
    upon receiving an instruction from the operator, capturing a face image of the patient, and storing the face image in the memory component of the portable computing device as part of the patient file;
    receiving a measured size of the maxillary central incisors of the patient and storing the measured size in the memory component of the portable computing device;
    retrieving an image of two front teeth from the memory component of the portable computing device;
    displaying the image of two front teeth as part of the skull image on the screen of the portable computing device, wherein the size of the two front teeth is based on the measured size of the maxillary central incisors of the patient;
    upon receiving an instruction from the operator, moving and scaling the face image into alignment with the skull image and the image of the two front teeth; and upon receiving an instruction from the operator, capturing a composite image of the face image and the skull image, and storing the composite image in the memory component of the portable computing device as part of the patient file.

8. The method as recited in claim 7, and further comprising the step of:
upon receiving an instruction from the operator, adjusting the opacity of the face image, the skull image, or both the face image and the skull image as displayed on the screen of the portable computing device.

9. The method as recited in claim 1, and further comprising the step of:
displaying a tooth chart on the screen of the portable computing device; and
receiving an identification from the operator as to which upper teeth of the patient touch which lower teeth of the patient, and storing the identification of which upper teeth of the patient touch which lower teeth of the patient in the memory component of the portable computing device as part of the patient file.

10. A method of aligning a maxillary cast of a patient for producing a dental prosthetic for a patient using a portable computing device, comprising the steps of:
upon receiving an instruction from an operator, creating a patient file for the patient and storing the patient file in a memory component of the portable computing device;
upon receiving an instruction from the operator, using an image capture device of the portable computing device to capture an image of the patient, including the teeth of the patient;
displaying the image of the patient on a screen of the portable computing device;
retrieving a facial alignment image stored in the memory component of the portable computing device, wherein the facial alignment image includes a set of crosshairs;
displaying the facial alignment image overlaying the image of the patient on the screen;
aligning the set of crosshairs of the facial alignment image with the front teeth of the patient on the image of the patient;
upon receiving an instruction from the operator, capturing a face image of the patient, and storing the face image in the memory component of the portable computing device as part of the patient file;
displaying a tooth chart on the screen of the portable computing device;
receiving an identification from the operator as to which upper teeth of the patient touch which lower teeth of the patient, and storing the identification of which upper teeth of the patient touch which lower teeth of the patient in the memory component of the portable computing device as part of the patient file;
upon receiving an instruction from the operator, using the image capture device of the portable computing device to capture an image of a maxillary cast of the patient positioned on a universal occlusal stand;
retrieving the face image of the patient from the patient file;
displaying the face image of the patient overlaying the image of the maxillary cast on the screen of the portable computing device;
aligning the image of the maxillary cast with the face image of the patient;
mounting the maxillary cast and a mandibular cast of the patient on an articulator; and
comparing which teeth of the maxillary cast and the mandibular cast touch to the identification of which upper teeth of the patient touch which lower teeth of the patient.

\* \* \* \* \*